(12) United States Patent
Rees

(10) Patent No.: US 8,933,426 B2
(45) Date of Patent: Jan. 13, 2015

(54) SYSTEM AND METHOD FOR PROVIDING A SUSPENDED PERSONAL RADIATION PROTECTION SYSTEM

(71) Applicant: Interventco, LLC, Dallas, TX (US)

(72) Inventor: Chet R. Rees, Dallas, TX (US)

(73) Assignee: Interventco, LLC, Dallas, TX (US)

( * ) Notice: Subject to any disclaimer, the term of this patent is extended or adjusted under 35 U.S.C. 154(b) by 0 days.

(21) Appl. No.: 14/064,975

(22) Filed: Oct. 28, 2013

(65) Prior Publication Data

US 2014/0054474 A1    Feb. 27, 2014

Related U.S. Application Data

(63) Continuation of application No. 12/688,353, filed on Jan. 15, 2010, now Pat. No. 8,598,554, which is a continuation-in-part of application No. 12/099,077, filed on Apr. 7, 2008, now Pat. No. 7,973,299.

(60) Provisional application No. 61/022,174, filed on Jan. 18, 2008.

(51) Int. Cl.
*G21F 3/02* (2006.01)
*A61B 6/10* (2006.01)
*A61B 6/00* (2006.01)

(52) U.S. Cl.
CPC . *G21F 3/02* (2013.01); *A61B 6/107* (2013.01); *A61B 6/4423* (2013.01)
USPC ..................................... 250/516.1; 250/519.1

(58) Field of Classification Search
USPC ................. 250/516.1, 519.1, 515.1
See application file for complete search history.

(56) References Cited

U.S. PATENT DOCUMENTS

| | | | |
|---|---|---|---|
| 1,636,419 A | 7/1927 | Hollander |
| 2,718,598 A | 9/1955 | Graf |
| 2,794,128 A | 5/1957 | Shasky |
| 3,308,297 A | 3/1967 | Mansker |
| 4,197,720 A | 4/1980 | Nani |
| 4,254,341 A | 3/1981 | Herr et al. |
| 4,286,170 A | 8/1981 | Moti |
| 4,581,538 A | 4/1986 | Lenhart |
| 4,654,188 A | 3/1987 | Hankinson |
| D300,945 S | 5/1989 | Fleming et al. |
| 4,843,641 A | 7/1989 | Cusick et al. |
| 4,932,079 A | 6/1990 | Bridgewater |
| 5,006,718 A | 4/1991 | Lenhart |
| 5,015,864 A | 5/1991 | Maleki |

(Continued)

FOREIGN PATENT DOCUMENTS

DE    29 34 955 A1    3/1981

*Primary Examiner* — Kiet T Nguyen
(74) *Attorney, Agent, or Firm* — Scott L. Harper; Harper Washam LLP

(57) ABSTRACT

An improved personal radiation protection system that substantially contours to an operator's body is suspended from a suspension means. The garment is operable to protect the operator from radiation. The suspension means is operable to provide constant force and allows the operator to move freely in the X, Y and Z planes simultaneously, such that the protective garment, face shield, illumination means or other attachments integrated the system are substantially weightless to the operator. A face shield and arm cover can also be incorporated with the system, such that the face shield and arm cover are substantially weightless to the operator. The suspension means may be mounted to the ceiling, a vertical wall, the floor, or on a mobile platform.

17 Claims, 16 Drawing Sheets

(56) References Cited

U.S. PATENT DOCUMENTS

| | | |
|---|---|---|
| 5,115,140 A | 5/1992 | Rodriguez |
| 5,274,851 A | 1/1994 | Simpkins et al. |
| 5,623,948 A | 4/1997 | Van Morris |
| 5,626,540 A | 5/1997 | Hall |
| 5,704,881 A | 1/1998 | Dudley |
| 5,772,622 A | 6/1998 | Friske |
| 5,978,960 A | 11/1999 | Wrightman |
| 5,981,964 A | 11/1999 | McAuley et al. |
| 6,194,860 B1 | 2/2001 | Seelinger et al. |
| 6,281,515 B1 | 8/2001 | Demeo et al. |
| 6,448,571 B1 | 9/2002 | Goldstein |
| 6,459,091 B1 | 10/2002 | Demeo et al. |
| 6,653,648 B2 | 11/2003 | Goldstein |
| 6,828,578 B2 | 12/2004 | Demeo et al. |
| 6,841,791 B2 | 1/2005 | Demeo et al. |
| 6,954,968 B1 | 10/2005 | Sitbon |
| 7,000,616 B2 * | 2/2006 | Diaz et al. ............ 128/889 |
| 7,273,006 B2 | 9/2007 | Rasmussen et al. |
| 7,319,400 B2 | 1/2008 | Smith et al. |
| 7,476,889 B2 | 1/2009 | Demeo |
| 7,608,847 B2 | 10/2009 | Rees |
| 7,973,299 B2 | 7/2011 | Rees |
| 2009/0256044 A1 | 10/2009 | Miller et al. |

* cited by examiner

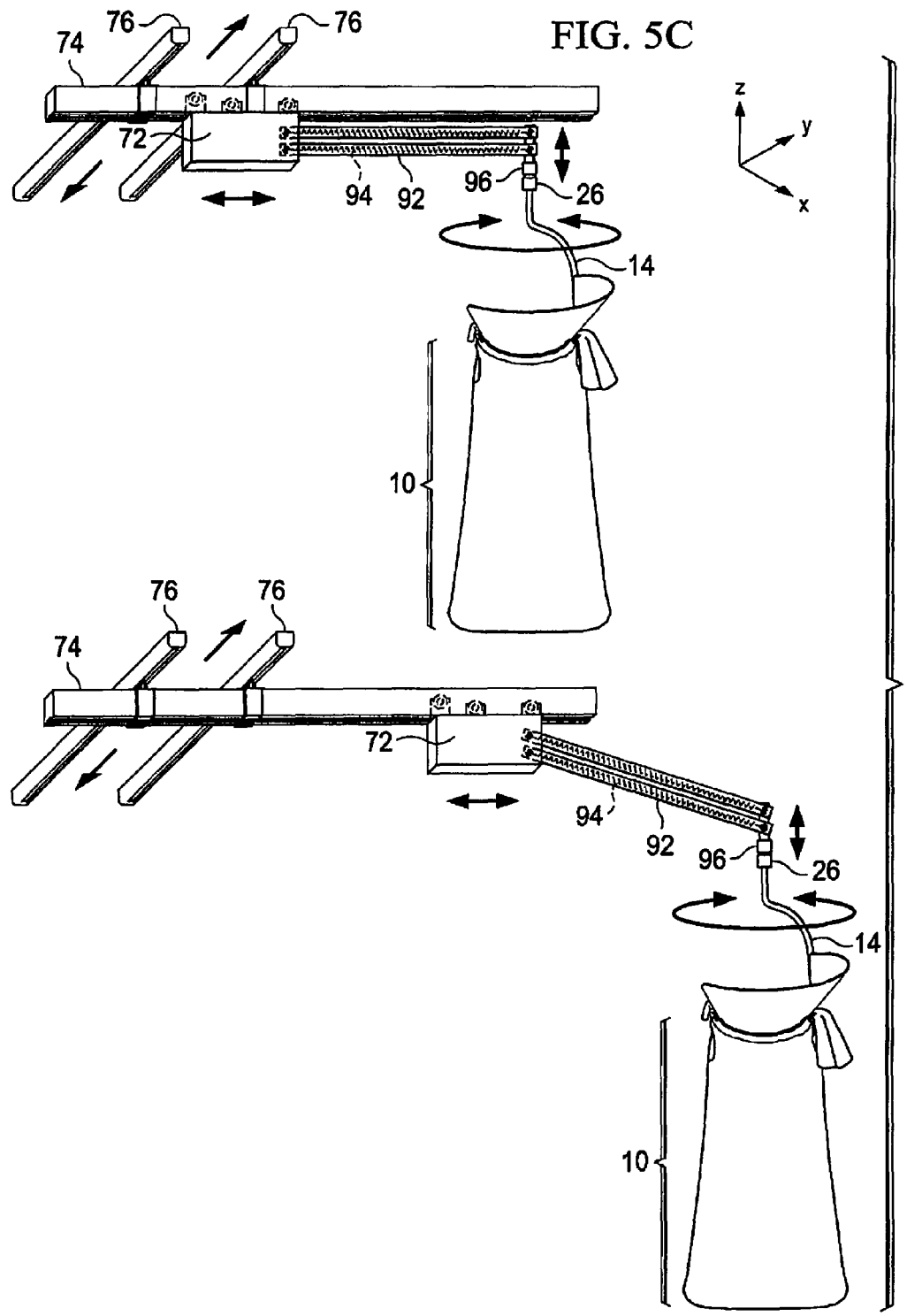

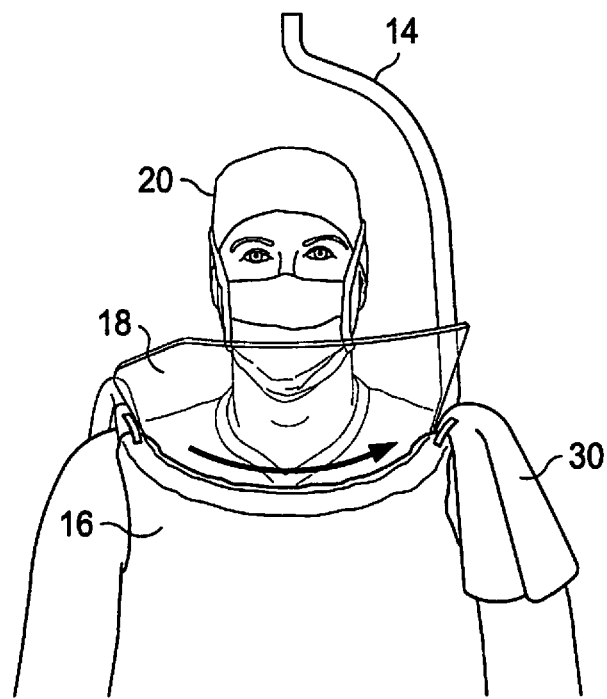
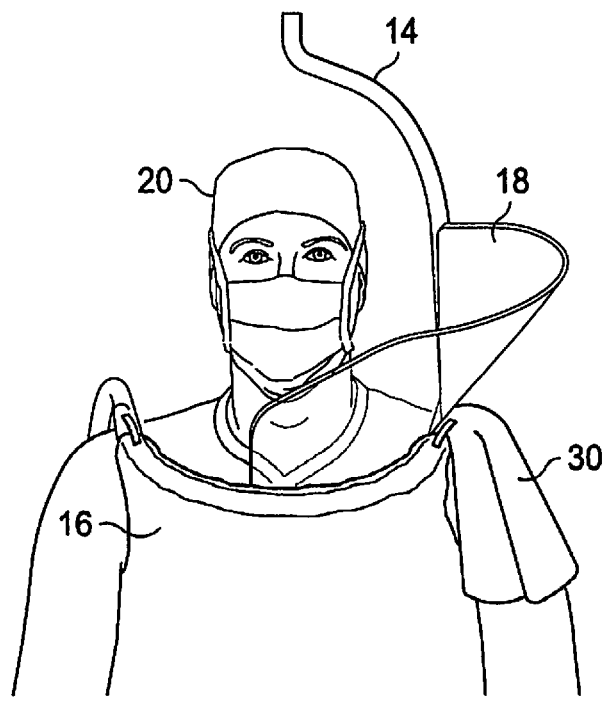
FIG. 6G

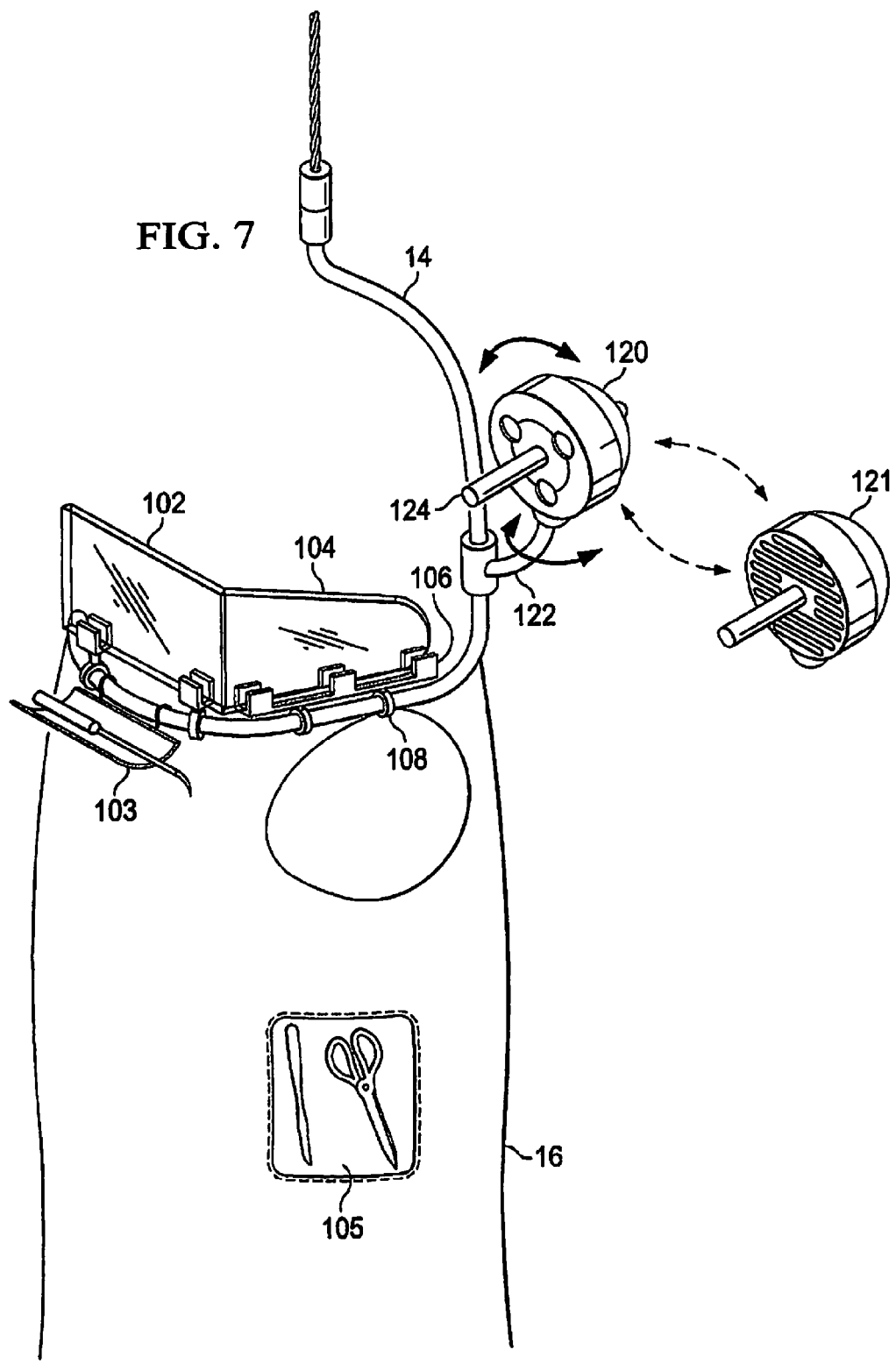

SYSTEM AND METHOD FOR PROVIDING A SUSPENDED PERSONAL RADIATION PROTECTION SYSTEM

CROSS-REFERENCE TO RELATED APPLICATIONS

This application is a continuation application and claims the benefit of and priority to co-pending U.S. patent application Ser. No. 12/688,353, filed on Jan. 15, 2010, which claims the benefit of and priority to U.S. patent application Ser. No. 12/099,077, filed on Apr. 7, 2008 and which issued as U.S. Pat. No. 7,793,299, and the benefit of and priority to U.S. provisional patent application Ser. No. 61/022,174, filed on Jan. 18, 2008, the disclosures of which are hereby incorporated herein by reference.

TECHNICAL FIELD

The present invention relates in general to radiation protection and, more particularly, to a suspended personal radiation protection system.

BACKGROUND OF THE INVENTION

Radiation is used to perform many medical diagnostic and therapeutic tests and procedures. Medical, veterinary, or research personnel may be involved in the performance of these tests and procedures. These professionals are being exposed to scattered radiation as they perform their work. The long-term effects of this exposure are poorly understood at the present time, but are considered serious enough to warrant mandatory protection for operators, who are required to wear garments or barriers that contain materials, which absorb a significant proportion of the radiation. In order to properly perform tests or procedures on patients, operators require freedom of motion. Providing a personal radiation protection system and method that properly protects operators, while allowing operators to move freely and comfortably, presents a significant challenge for operators in radiation environments.

SUMMARY OF THE INVENTION

In accordance with the present invention, a method, a system, and an apparatus for implementing a suspended personal radiation protection solution are provided that substantially eliminate or reduce the disadvantages and problems associated with previous approaches.

According to one embodiment of the present invention, a system for offering radiation protection includes a garment that contours to an operator's body. The garment protects the operator from a substantial portion of radiation which is scattered about during a treatment or testing procedure. The garment is supported by a frame connected to a suspension system that reduces a portion of the garment weight on the operator. A binder system may be provided which allows the operator to enter the radiation protection system, remain in proximity to the protection system while conducting a test or procedure, and then exit from the protection system without the loss of sterility.

According to another embodiment of the present invention, the binder system comprises a ball and cup attach/detach mechanism. A harness or belt is secured to the operator. The harness or belt includes a binding component, such as a spherical ball capable of being mated with a corresponding binding component such as a cup or socket attachment point affixed to the radiation protection system. The operator positions the ball in appropriate proximity with the cup resulting in the ball and cup mating thereby detachably securing the operator to the radiation protection system. When the operator desires to disengage from the radiation protection system, the operator need simply overcome the relatively small coupling force maintaining the mated connection between the ball and cup connection without losing sterility. Alternative embodiments of a binding system are disclosed herein which include the use of mechanical binding systems, friction binding systems, magnetic and electromagnetic binding systems as are commonly known in the art.

According to another embodiment of the present invention, the radiation protection device includes a suspension assembly with an extension arm. The extension arm may also include a counterbalance or tension mechanism to offset the weight of the garment, face shield and frame supporting the garment. The extension arm improves the range of motion afforded to the operator while using the personal radiation protection device and the responsive motion of the suspension component to the movements of the operator.

According to another embodiment of the present invention, the radiation protection device includes a configurable face shield. The face shield may include an adjustable front plate and adjustable side plate attached to the frame and configured to provide optimal shielding to the operator's face and neck area. The face shield is securably detachable to the frame, and while attached to the frame, the front plate and/or side plate may be independently oriented into an appropriate position relative to the operator. The side plate may be removed, inverted, or placed on the right or left side of the front plate, so as to provide optimal protection to the operator's head and neck while performing tests or procedures.

According to another embodiment of the present invention, the radiation protection device includes a lighting component, or lamp. The lighting component may be attached to the suspension assembly or frame as desired by the operator or the demands of the environment where the radiation protection device will be utilized. The lighting component may be mounted so as to be adjustable and may be configured to maintain relatively constant orientation with the operator. Adjustments may be possible by the operator by manipulation of a sterile handle or a sterile draped handle. Depending on the mounting location of the lighting component, the weight of the lighting component may be used as a counterbalance to advantage the mechanics of the system.

According to another embodiment of the present invention, the radiation protection device includes an instrument holder for holding instruments, tools or other objects which are used by the operator during tests or procedures. The instrument holder may be detachably secured to the suspension assembly, frame or garment. The instrument holder may be a tray, a pouch or a magnet, or any combination of such, which acts to hold instruments or other objects as desired by the operator.

According to another embodiment of the present invention, the radiation protection device includes environmental controls for adjusting and maintaining a comfortable environment for the operator while utilizing the radiation protection system. Environmental control mechanisms which may be detachably secured to, or rigidly attached, to the radiation protection system include fans or air blower systems to provide cooling to the operator. Thermoelectric heating elements located in close proximity to the garment may also be integrated into the personal radiation protection system to provide a heat source to the operator as known in the art.

Other technical advantages of the present invention will be readily apparent to one skilled in the art from the following figures, descriptions and claims. While specific advantages and embodiments have been enumerated above, various embodiments may include all, some, or none of the enumerated advantages.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 5C is a perspective view depicting an extension arm with a tension mechanism providing a balancing force for the personal radiation protection system in various spatial positions in accordance with the present invention;

FIG. 6G is a perspective view depicting an alternative embodiment of the adjustable face shield in accordance with the present invention;

FIG. 7 is a perspective view depicting a lighting component affixed to the personal radiation protection device in accordance with one embodiment of the present invention;

DETAILED DESCRIPTION OF THE INVENTION

Figure 1:
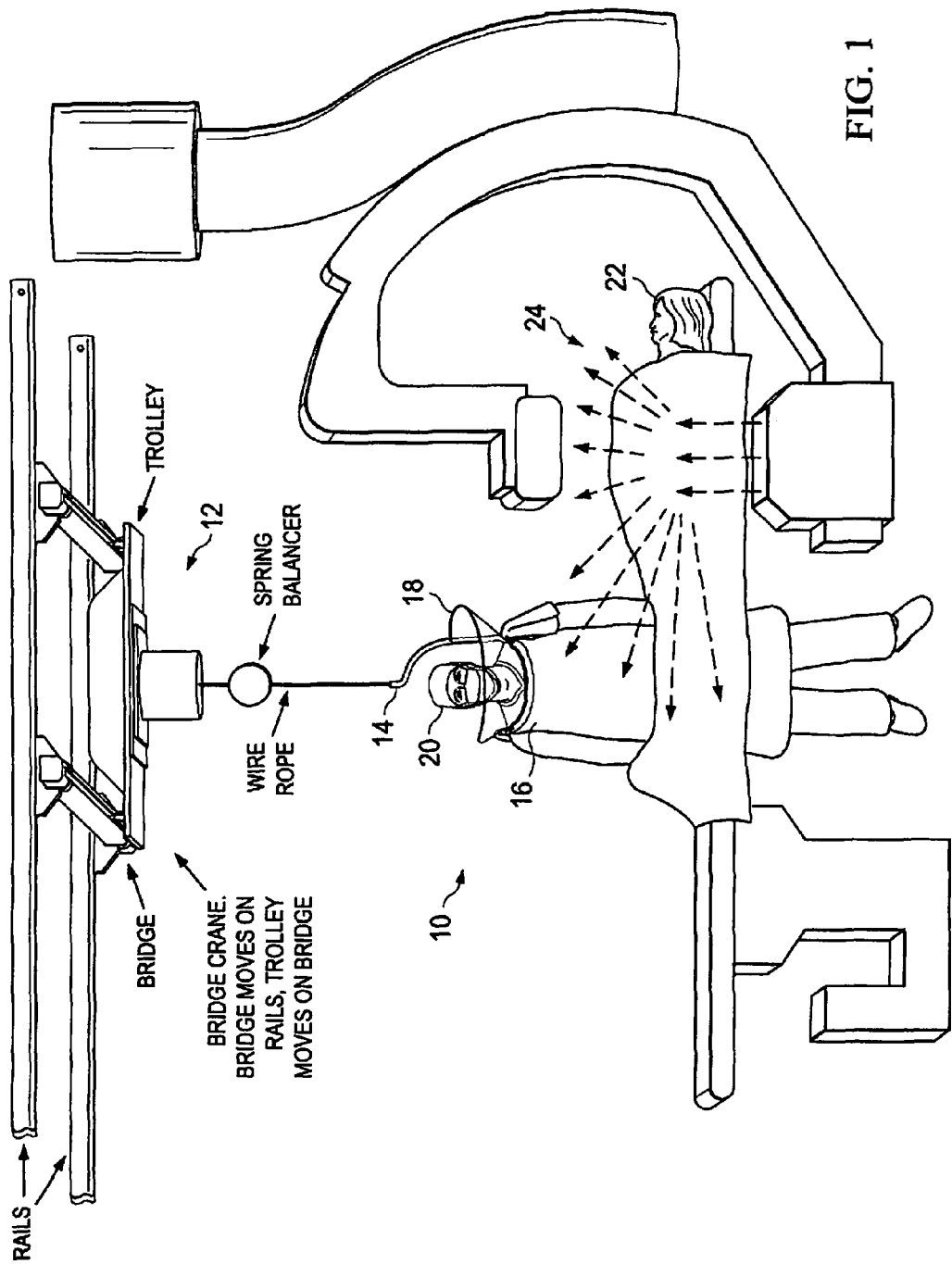
FIG. 1 is a perspective view of a suspended personal radiation protection system in accordance with the present invention.

For purposes of teaching and discussion, it is useful to provide some overview as to the way in which the invention disclosed herein operates. The following information may be viewed as a basis from which the present invention may be properly explained. Such information is offered for purposes of explanation only and, accordingly, should not be construed to limit the broad scope of the present invention and its potential applications.

Radiation is used to perform many medical diagnostic and therapeutic tests and procedures. The human patient or animal is subjected to radiation using minimal doses to enable completion of the medical task. Exposures to radiation are monitored to prevent or reduce risks of significant damage. Medical, veterinary, or research personnel may be involved in the performance of such procedures in great numbers.

Over many years, these professionals are being exposed to scattered radiation as they perform their work. Although their daily exposure is generally less than that for the patient, there are adverse cumulative effects to the operators. These long-term effects are poorly understood but are considered serious enough to warrant mandatory protection to workers in the form of garments or barriers that absorb a significant proportion of the radiation. There is a wide variety of such barriers commercially available, but these solutions have significant limitations for the operators who must come in close contact with the subject. These operators may be physicians and their assistants, or technically skilled medical personnel, who perform simple or complex medical procedures using their bodies and hands in proximity of the patient. In many cases, scatter radiation from the subject or physical elements in the direct radiation beam will pose significant health risks and unacceptably high exposure.

Risks of radiation exposure at the levels of medical personnel include cancers, cataracts, skin damage, etc. A review of current protective systems outlines their limitations. Radiation-absorbing walls are useful to contain the radiation to a room, but do not prevent exposures within their confines. Barriers within the room, such as floor or ceiling supported shields, are effective at blocking radiation for personnel who are not in close contact with the radiation field, such as some nurses and technologists, but must be positioned or repositioned frequently when personnel move around the room. They also provide cumbersome interference for operators performing the actual medical procedure. They may also be difficult to keep sterile when attempting to use them within the sterile field.

The most commonly used protection for operators involves the use of garments containing radiation-absorbing materials, generally lead or other metals, which are worn in the fashion of a coat, smock, skirt, or vest, and do not contaminate the sterile field because they are worn underneath the sterile covering gown. These garments are heavy and uncomfortable, and their long-term usage is known to be associated with diseases of the spine, especially the neck and back, knee disorders, and other musculoskeletal problems, which can result in disability, medical expenses, and decreased quality of life for the operator.

The trade-off between protection and garment weight results in the frequent use of garments that do not cover the legs, head, torso, and eyes optimally, and may provide suboptimal radiation protection due to the thickness of the metallic material being limited by the tolerability of the operator. To protect other radiation-sensitive tissue such as the corneas of the eye and the thyroid, special heavy glasses containing metallic compounds and a collar around the neck are often worn. Even when the operator is encumbered with these items, the base of the skull which may contain sensitive bone marrow and the face are still unprotected. Personal face and neck shields address this problem, and are commercially available, but are rarely worn due to their cumbersome nature and heavy weight.

Such problems have been present for many years with various attempts to solve them. For example, modifications to floor-supported mobile shields attempt to provide improved dexterity for the operator relative to the standard bulky mobile barrier, and a floor support system with a modified garment design also attempts the same. However, they still act as obstacles to the free movement of the operator using them. Another system of barriers (such as those referred to as radio-protective cabins) around the patient has been proposed, but that appears cumbersome, confining, and inhibitory to operator movement both gross and fine, patient/subject contact, and sterile field operation.

Ceiling mounted barriers around the patient also limit contact between patient and operator, and may make control of a sterile field difficult. One configuration includes a ceiling mounted device, which supports the weight of a lead garment, involving a dolly, or trolley, movable in one linear axis, with or without an extension arm that rotates around a central point on the dolly. Such mechanical configurations are in place for other types of suspended barriers and their motion mechanics may not be well suited for use with something attached to the operator's body since the operator must frequently move rapidly and freely in all three spatial axes. Typically, the operator will walk in unpredictable and rapid patterns over an operating area. One configuration includes the garment being suspended by a simple expansion spring, which will provide uneven forces on the shield and operator depending on its degree of expansion occurring with operator motion due to the nature of its simple spring mechanics. It may also result in harmonic motions that affect operator dexterity. In addition, failure of the spring due to cycle stresses could lead to operator injury. Likewise, location of the spring in a vertical direction above the operator results in movement limitations due to ceiling height. Integration of the system with the heavy image intensifier monitor screen would further encumber the operator from normal motion.

A discussion of the types of motion performed by operators during their work is relevant. Operators generally stand next to an operating table where the patient is positioned. They often reach over the patient to various parts of the body, and they may lean forward while reaching for items, surfaces, etc. This puts stress on the operator's spine when heavy garments are worn. They may bend or stoop, but usually only to a small degree because the workplace containing the patient limits vertical motion. In addition, most procedures involve a sterile field where the operator's hands, arms, and torso must remain confined, so excessive vertical motion is prohibited. The operator may need to move considerably in all three spatial planes by walking or turning their body. Clearly, the operator requires freedom of motion in each of these directions to perform a procedure or test.

Overhead cranes have been available for many years and are commonly employed in the materials-handling industry. The following is a description of a bridge crane. A bridge crane includes at least one bridge, and a trolley moving on the bridge, end trucks arranged at the ends of the main bridge to support the main bridge, and wheels arranged to the end carriages intended to move along substantially parallel rails substantially parallel to the end trucks. In some embodiments, articulated end trucks provide increased maneuverability for the bridge so as to allow the bridge to rotate or sway, while staying safely attached to the rails. Smaller cranes such as those to be used to support a load up to 250 pounds are often operated by workers without the aid of motorized assistance because the crane's movable parts are light enough to be manipulated by hand. Different systems are employed to suspend the load from the cranes, including hoists, balancers, and intelligent assist devices as known in the art.

Tool balancers are also currently available and help to suspend tools in the workspace in a manner that provides ergonomic benefits for the workers using them. The tool balancer is generally attached over the workspace, and reels out cable from which the tool is suspended. Adjustments may be made to provide a "zero gravity" balancing of the tool at the desired height such that the worker may move the tool up or down within a working range without having to bear a significant portion of the tool's weight. Adjustments may cause the tool balancer to exert a stronger upward force such that the operator must apply a downward force on the tool to pull it down to the workspace and the balancer will cause the tool to pull it down to the workspace and the balancer will cause the tool to rise when the operator releases it.

Tool balancers may be of the spring, hydraulic or pneumatic variety, referring to the force mechanism, which provides the balancing force for its operation. A spring tool balancer, such as in one embodiment of the invention disclosed herein, generally contains a coiled flat spring, which is attached to a reel with a conical shape and which serves as the platform for the winding of the cable. The conical shape provides a variable mechanical advantage, which offsets the variance of the force provided by the spring as it winds or unwinds. The result is a relatively constant force on the cable within a definable working range.

Safety concerns mainly involve falling objects, strength of the suspension device, strength of the cable, and operator falls. The balancer can be attached to the trolley by its own hook and a safety chain. The suspension device is commercially available at specified maximum loads, which include a wide safety margin. The mounting of the suspension device is accomplished according to architectural/engineering requirements and standards for suites where the present invention is to be utilized.

Tools or other loads may also be balanced by arms that provide torque approximately equal to the weight of the load via various mechanical systems including internal cables and pulleys with springs, pneumatic force, or counter-weights. Such arm systems could be manipulator arms, torque arms, reaction arms, or balancing arms as are known in the art.

Detachment of the frame and/or garment from the suspension system will require certain care. A cable stop on a conventional tool balancer will prevent the hanger from going higher than the set level. Some balancers are equipped with a locking mechanism that prevents motion of the cable during load change or removal. This permits simple removal or exchange while standing at ground level. Alternatively, without activating a locking mechanism, the operator could raise the load upwards until it contacts the balancer stop, or until the arm is fully raised to its capacity in the case of an arm system, and then remove the garment without concern for sudden upwards, uncontrolled motion of the balancer cable or arm and attached components. Alternatively, a weight, which is approximately equivalent to the weight of the supported system, could be attached to the cable, rod, or arm prior to disengaging the supported system. This would act to "drop" the supported system and require it to be supported by the operator, who may then disengage it from the cable, rod or arm system. The weight will prevent any upward motion of components in an uncontrolled manner. The next time the frame and/or garment is attached, the weight could be removed after secure attachment of the supported load is confirmed.

For most operational scenarios, the protection system need not be detached from the suspension system (e.g. cable, rod, or arm supporting the system). In alternative embodiments, it may be left suspended and simply moved out of the way of other activities. Another alternative method would involve setting the force on the tool balancer or balancing arm to be slightly greater than the weight of the suspended shielding components. Once removed from the body, the suspended protection system would then slowly and safely rise up until stopped by the stop mechanism. Upon next use, it could be easily pulled back down into position by the operator. Annual inspections of the system may be performed for cable frays, hook or lock malfunctions, and suspension component flaws.

In the event of an operator fall, it is unlikely that the system will contribute to operator harm since in some embodiments the suspension system allows the operator to reach the floor without restriction. In view of the embodiments disclosed herein, the design of the system provides for the safe and quick detachment of the operator from the radiation protection system. The binder system quickly provides engagement/disengagement from radiation protection system as the binding forces keeping the operator in proximity to the radiation protection system would be easily overcome by the forces exerted during a fall.

In the event of malfunction, many support systems are equipped with automatic locking mechanisms to prevent dropping of the load supported by the support system. In the event of actual detachment, the frame supporting the suspended shielding components may be designed such that there are pads positioned over the shoulders of the operator which would gently engage the operator's shoulders to support the weight of the device in the event of a suspension failure. However, this type of malfunction would be rare as it would generally be avoidable with adequate support structure strength and annual inspections of the entire system.

In the event that rapid detachment of the operator from the system is necessary due to emergency, the binding system disclosed herein is designed to provide simple and quick disengagement between the operator and the radiation protection system. As disclosed further herein, a simple hand push or wave or actuation of a switch by the operator or another in various embodiments results in the operator disengaging quickly and safely from the radiation protection system without detachment of the garment from the system. The garment can be left hanging on the system and then moved clear of the patient or stretcher. Likewise, the operator can quickly disengage from, and then reengage with, the system while remaining sterile.

Turning back now to the general problem of radiation, it is evident that people are often exposed to radiation in the course of their work. The proposed concept, outlined herein, describes a device and technique intended to address many of the aforementioned problems. It provides substantial shielding for the operator: covering a large part of the body. The shielding capacity can be increased with thicker layering of heavy metal or other radiation-protective material, thus reducing the stress on the operator because the device is substantially weightless to the operator. The device is close to the body of the operator, much like a conventional apron, but it is not supported by the operator. It moves with the operator as he/she moves around within the working field and sterile field, and allows movement of arms and body parts to accomplish the procedure at hand.

The overall benefits of the device include: improved comfort for the operator who is no longer supporting heavy-shielding clothing, improved radiation protection to an operator through a much greater portion of body shielding compared to a conventional apron, as well as more effective shielding of much of the covered body parts due to greater use of the shielding material. This approach also offers a musculoskeletal benefit due to the absence of a significant weight burden on the operator.

Turning now to the figures, FIG. 1 is a perspective view of a radiation protection system 10. System 10 includes a suspension assembly 12, a frame 14 for supporting a radiation protection garment 16, and a face shield 18 in the embodiment shown. Operator 20 utilizes system 10 for the purposes of providing protection to the operator during a procedure performed on patient 22 using radiation rays 24. The protection system 10 may be easily installed or integrated into a typical operation suite.

In general, the garment 16 is suspended from the suspension assembly 12 and supported by frame 14. Frame 14 contours around the shoulders, chest and torso of the operator 20 and supports the garment 16 and/or face shield 18, along with other potential devices or instruments such as an instrument tray, lighting apparatus, environmental control or other instrumentation which may easily be integrated with system 10 as described hereafter. In one embodiment shown in FIG. 1, frame is connected with the suspension assembly 12 wherein the suspension assembly may include a rigid rod, a wire rope, an extension arm, or other suspension means discussed herein. Multiple wire ropes, reaction arms, tool balancers, trolleys and bridges, and other various support systems as are known in the art, may be utilized for supporting the radiation protection systems and embodiments shown herein as appropriate and desired by the user or facility where the system will be utilized.

Figure 2:
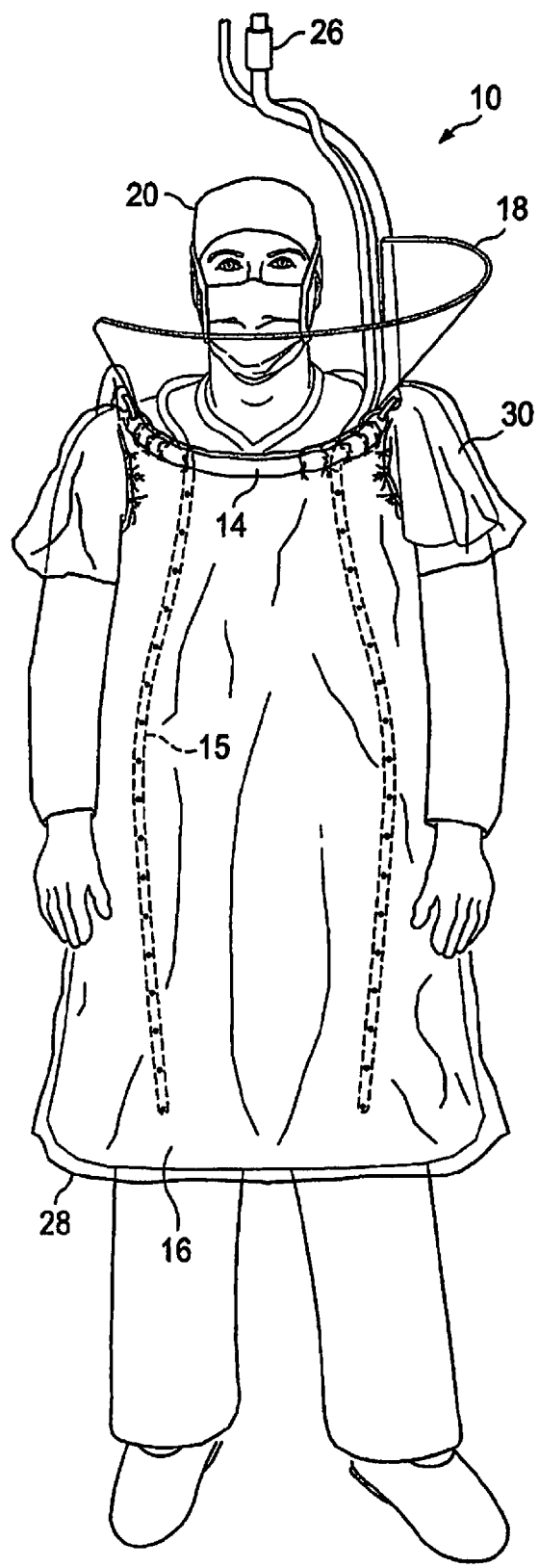
FIG. 2 is a close up perspective view of a personal radiation protection system in accordance with the present invention.

FIG. 2 further illustrates the frame and garment architecture. The protection system 10 is shown with frame 14 which contours around the neck, shoulders and upper torso of the operator 20. In one embodiment, the frame 14 is open in the back to permit rear entry into the system 10 by the operator 20. Frame 14 supports garment 14 and is detachably connected to the suspension system 10 (as shown in FIG. 1) via hanger 26. It should be noted that hanger 26 may be an attachment mechanism using attachment means as known in the art, including but not limited to, threaded connectors, hook and rings, or and/or screw type connectors. Hanger 26 may also be a rigid, rotatable or swiveling connector as required by the operational mandate for the system 10. In still other embodiments, the frame 14 includes an attachment means for connection to the suspension assembly, without the requirement of hanger 26. The depicted embodiment allows the operator 20 to position herself in proximity with, or behind, the garment 16 such that the operator 20 is not supporting the weight of the garment 16 or frame 14. In this sense, she is liberated from the typical and problematic weight constraint of typical radiation garments and protection systems. The frame 14 and garment 16 are constructed to allow unimpeded rear entry to the radiation protection system by the operator 20 without the need to manipulate the frame 14 or the garment 16 to engage with the system 10. In some embodiments, engaging with the system simply requires the operator to come into proximity with the frame 14, such that the frame 14 and operator 20 remain in proximity due to the operator's arm(s) and/or torso being in relative contact with the frame 14 and/or garment 16. In other alternative embodiments, frame 14 may be constructed as a shaped, rigid unit or may be constructed of semi-rigid, flexible materials allowing the operator 20 to manipulate the shape of the frame 14 to suit her body shape. Manipulation of frame shape can also be provided by the use of rigid frame materials connected by joints of many different types including torque hinges, or friction hinges, which are somewhat similar to conventional door hinges with friction in their movement, often designed to specifications or adjustable, that enable the frame to keep the desired shape, once set, until sufficient force is again applied to overcome the friction. In other alternative embodiments, the operator 20 will engage with system 10 using a binding system disclosed herein, or by the manipulation of a belt system, or activation of a mechanism that manipulates a belt system. Such a belt system would encircle or partially wrap around the operator for enhanced fit or function. The invention herein is different from conventional aprons or vests and previous suspended aprons which have more conventional shoulder constructions that required the garment arm hole to be opened up somewhat or lifted or manipulated in some way for the operator to gain entrance. This can be a problem with sterile entry and exit of an operator wearing a sterile gown and trying to engage a device wrapped in a sterile drape. The rearward openness of system 10 aids in these maneuvers without contamination of the sterile operator or field that is another novel aspect of the invention disclosed herein. Further, once the operator has engaged the device such close proximity to the frame 14 and garment 16 can result in uncomfortable body temperatures on the part of the operator. To correct this effect the garment 16 may feature an environmental control system consisting of ducting 15 that directs cooled or heated blown air to the operator from a supply line supported by the frame and hanger 26.

Some embodiments of system 10 disclosed herein are shaped to require no user manipulation and do not require a change in shape to enter, use, and exit from the system. In various alternative embodiments, the frame 14 and garment 16 may be shapeable, which can be accomplished with or without the presence of the operator's body. Some of the unique features of the invention disclosed herein spring from the novel frame 14 which is generally positioned in front of the operator 20 during use. Frame 14 may be constructed from rigid, jointed, semi-rigid and/or flexible material to allow frame 14 to be shaped or to be fashioned to substantially contour with the operator 20. In one embodiment, frame 14 is semi-rigid and can be shaped to substantially contour to the body of a particular operator. When the system 10 is used by another operator 20 of different body size, the frame 14 may be reshaped to adjust the contour to the body size of the next operator 20. As depicted in FIG. 2, the frame 14 sweeps in front of the operator 20 from one side to the other, acting as a support for the garment 16 and providing form and structure to the garment 16 in the areas near the operator's head, shoulders, arms, and upper body, where important movement occurs during a procedure. It also serves as a mechanism to assist in the proper balance of the entire system 10 so as to maintain proper operational orientation. Previously described suspended protection systems typically attach at the shoulders of the operator without providing a frontal frame element that performs the functions described herein. Frame 14, combined with the disclosed suspension system 12 and various other support alternatives discussed herein, allows concentration of the mass and weight of the system 10 towards the front and sides of the operator 20, while maintaining proper balance and orientation relative to the operator 20. This facilitates simple and effortless entry and exit of the operator from the system 10. It also permits secure attachment of a face shield 18 in front, and to the sides if needed, of the operator 20 while maintaining proper balance and orientation, without restricting the motion of the operator's body and arms when using the system. The shape desired by the operator 20 can be substantially maintained regardless of the operator's presence in the system, except allowing for some minor flexing of the arm flaps 30 and fabric as the operator 20 moves. However, no substantial shaping or change in form is necessary for the operator 20 to enter the device 10, thus facilitating sterile entry/exit. Also, a sterile drape 28 may be used to substantially cover garment 16 and portions of frame 14. Sterile drape 28 is easily inserted over the desired portions of garment 16 and frame 14 to provide additional sterile protection.

Another novel improvement disclosed herein, is that in some embodiments a circumferential belt or strap is not required to be fastened behind, around or in front of the operator; the operator is never completely surrounded by any continuous component as in conventional aprons and protection systems which use a belt that joins the apron between the shoulder blades or elsewhere to keep it on the operator. The invention disclosed herein may include embodiments that wrap completely around the operator's torso. Nonetheless and although the rear components may touch or overlap in some cases, some embodiments are maintained in this position by frame elements that are oriented so that opening and closing of the frame to allow entry of the operator does not require manipulations near the back of the system or operator, or the passage of any straps or belts around the rear of the system or operator. The invention disclosed herein includes embodiments that eliminate this need by providing a frame structure that permits engagement to the operator without requiring a change in the frame shape or manipulation of belts or other components each time the operator engages or disengages from the system. In some embodiments, the operator is never surrounded by a component that must be disengaged upon entry or exit.

Additional alternative embodiments are envisioned wherein the rear frame or apron elements connect to each other, but this connection does not require manipulation of rear components, or passage of operator's or assistant's hands towards the rear. Such a previously described embodiment utilized a frame belt with a magnetic component in the rear that facilitated a binding of the rear components together once they are moved together in proximity to each other using manipulations performed at the sides or front. Although some alternative embodiments may include a flexible belt or tie that connects the rear frame or apron elements in the rear, or wraps around the body in a manner similar to a kitchen apron or conventional clothes garment, many alternative embodiments are described that permit partial or complete circumferential enclosure of the frame or apron around the operator that eliminate the need for manipulation or passage of the hands rearward, thus facilitating rapid entry and exit, and more importantly facilitating the ability of an operator wearing a sterile gown to enter and exit the device that is also protected by a sterile cover, in a manner where sterility is not broken by the passage of non-sterile objects, or use of objects that are difficult to drape, or the use of an assistant or the passage of operator's hands out of the conventional sterile field.

Frame 14 provides a shape for the garment of generally an arc or curve that accommodates the shape of the operator's body, whereas previous known suspended garment systems assumed their contoured shape upon engagement with the operator, by being flexible without any predetermined shape, and without the ability to maintain the working shape in the absence of the operator's body. Previous suspended garment systems were basically suspended clothing, like an apron or shirt that were donned in similar manners to corresponding clothing articles, whereas the device disclosed herein utilizes a shaped rigid, or flexible in other embodiments, frame 14 to which flexible garment 16 material may be attached to allow the maintenance or molding of the frame to an appropriate and comfortable shape so that the operator can simply step into it, although in alternative embodiments the garment 16 material may be stiff or nonmalleable. The frame 14 may be attached to the suspension system 12 at one or multiple points as disclosed herein. In one alternative embodiment shown in the figures, unilateral suspension provides an unobstructed contra lateral side, while providing a more substantial support structure for greater strength. Additionally, while using radiation during a procedure or task, the operator 20 may freely move in the X, Y and Z spatial planes such that the frame 14, garment 16 and face shield 18 are substantially weightless to the operator 20.

Figure 3:
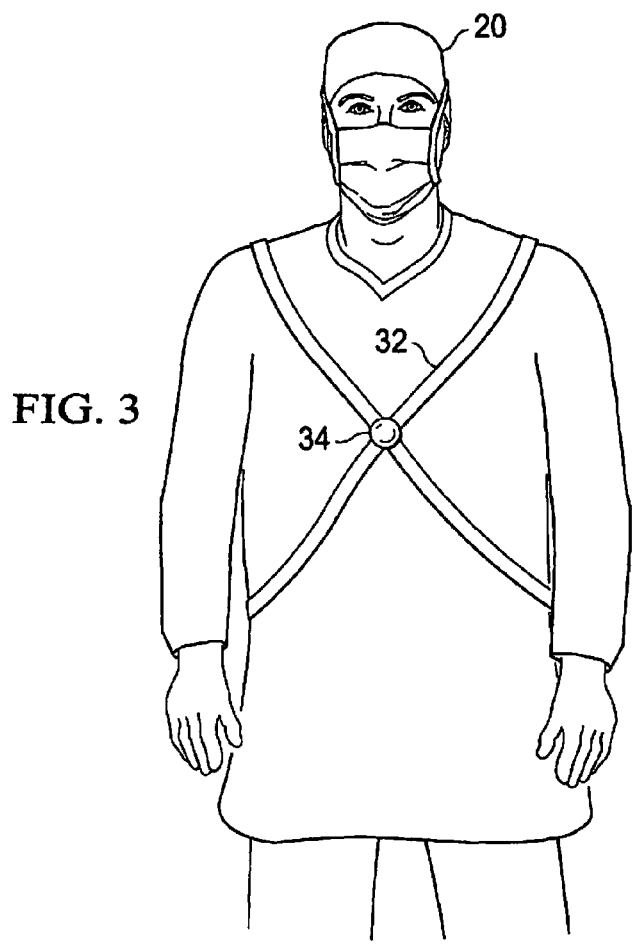
FIG. 3 is a perspective view of a harness component of the binding system in accordance with the present invention.

FIG. 3 depicts one embodiment of an engageable/disengageable binding system which is utilized for keeping the operator and the radiation protection system linked or connected in relative proximity together during a procedure. This embodiment depicts an operator 20 who has donned a harness 32, which may consist of a belt, vest, strap, garment or other structure capable of being detachably secured on or about the operator's person. Many different configurations are possible, including an embodiment that incorporates a wide waist belt that provides lumbar support. A first binding component, in the depicted ball 34, is secured to a location on the harness 32, with a second binding component (not shown) being secured to the frame, garment, hanger, or other attachment point to the radiation protection system as described herein. The harness 32 may be donned over the operator's sterile gown, or underneath the gown, as required. When the first binding component is engaged with the second binding component (see FIGS. 4A-4E) via friction, magnetic, electromagnetic, or by other mechanical binding mechanisms, the operator is secured to the personal radiation protection system so as to allow the operator and personal radiation system to move freely together in the X, Y and Z planes while maintaining operator proximity with and protection by the system. The binding mechanism may be designed and constructed to accommodate layers of fabric or plastic drape materials that may be present on the operator, such as a sterile gown, and on the device, such as a sterile drape. The binding mechanism(s) would bind together despite the interposed layer(s) without tearing or damaging the layers. When the operator disengages the first and second binding components, both component surfaces would remain covered by the drape, which would remain sterile since they were only in contact with other sterile materials. If sterilized binding components were used outside of the sterile drape, they would likewise remain sterile after disengagement.

FIGS. 4A-4E depict various embodiments of binding systems that serve to engage the radiation protection system to the operator so that it moves with her during operations. Depicted embodiments include various male-female connection mechanisms whereby the male and female components provide mechanical stabilization, flexible and/or rigid fixation between components that are attached to both radiation protection device and operator. In some embodiments, the male-female components also provide a guiding function, which facilitates the proper alignment of the binding components during engagement by the operator.

Figure 4A:
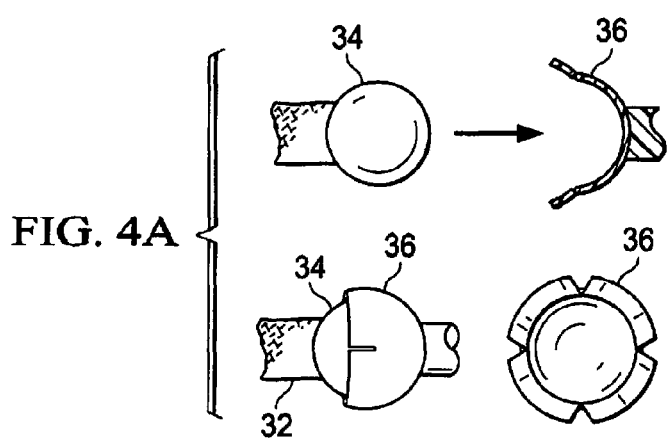
FIG. 4A is a side view illustrating the ball and cup binder system in accordance with the present invention.
Figure 4B:
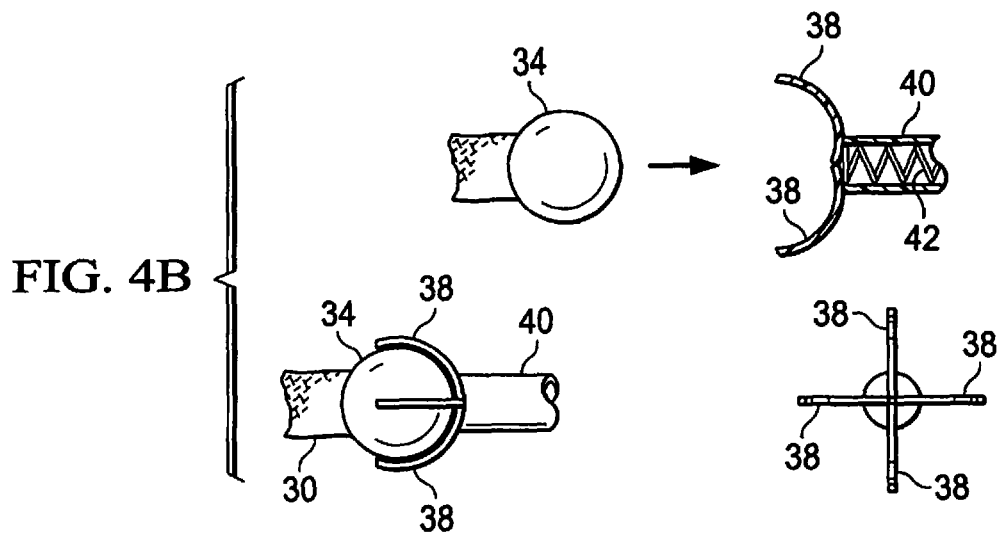
FIG. 4B is a side view illustrating an alternative ball and cup, or finger binder, system in accordance with the present invention.

FIGS. 4A and 4B show one embodiment of a binding system which utilizes a ball 34 and cup 36 connection. As shown in FIG. 4A, a first binding component, in this embodiment depicted as a ball 34, is attached to a harness 32 which is donned by the operator 20 as shown in FIG. 3. The second binding component, in this embodiment cup 36, is mounted to the garment or frame with the cup 36 shown in the "open" position. Depending on the mounting location of the second binding component cup 36 (e.g. to the frame 14 or garment 16 in various contemplated embodiments), the operator simply moves into relative position and ball 34 is received into cup 36 which to create an engageable/disengageable connection. The ball 34 and cup 36 connection allows the operator and the radiation protection system to move in relative, substantial unison with one another. In alternative embodiments, a variety of geometric shapes for binding components may be constructed so as to mate and have slightly different characteristics, such as multiple attachment sites on the frame, garment and/or operator, or binding components of lower and higher physical profiles as required by design and operational mandates. In various embodiments, the degrees of freedom of motion between the mated binding components may vary from none (such as a rigid connection), to limited within some rotational axes, to complete freedom of movement in all spatial directions. Different kinematic chains of articulation could be constructed to allow translational motion in addition to radial motion, and springs, gas springs, dampers, or other mechanical tensioning means could be employed. The binding system may be constructed so that a release mechanism must be activated to permit disengagement of the operator from the garment and/or frame, for example by operator hand movement or depressing a switch. Alternatively, it could be constructed such that a certain amount of forceful separation or specific rotational or translational movement would overcome the binding forces of the mated binding components and disengage the binding components without activation of other mechanical disengagement systems by the operator's hands or otherwise. This automatic disengagement function could be constructed for routine disengagement, or only as an emergency disengagement function, in one embodiment similar in function to the operation of a ski binding release mechanism. In other embodiments not shown herein, engagement could require activation of a mechanism, via an electronically controlled mechanism, while in other embodiments engagement would occur naturally as the components are pressed together.

In an alternative embodiment depicted in FIG. 4B, a second binding component attached to the protection system via rod 40, in this depiction a cup formed with articulating fingers 38 which when introduced into proximity with the first binding component, in this depiction ball 34, act to close around the ball 34, resulting in a flexible and/or rigid secure connection as desired between the first and second binding components. The articulating fingers 38 are held in a closed position forming the connection with the ball 34. In order to disengage from the connection between the ball 34 and cup fingers 38, the operator may activate a release mechanism which overcomes the spring 42 force holding the fingers 38 in the closed position around the ball 34, thus opening the fingers 38 and allowing the ball 34 to become detached, and allowing the operator to quickly and easily exit from the frame or garment. Alternatively, a more rigid connection between the first and second binding components may be fashioned by the use of lock and pin type connectors, magnetic, electromagnetic, key connectors, rigid plates, or other mechanical attachment means as known in the art.

In the embodiment shown in FIG. 4B, a spring 42 or other compressive/tensile force system could be used in conjunction with articulating fingers 38 to keep them in a closed cup position. When ball 34 is pressed into the cup formed by fingers 38, the maximum diameter of the ball 34 passes through the smaller diameter of the cup opening, prying the fingers 38 apart against the resistant spring force exerted by spring 42. Once the ball 34 and fingers 38 are in a mated position, the fingers 38 are closed around the ball 34 forming a connection between the first and second binding components.

Figure 4C:
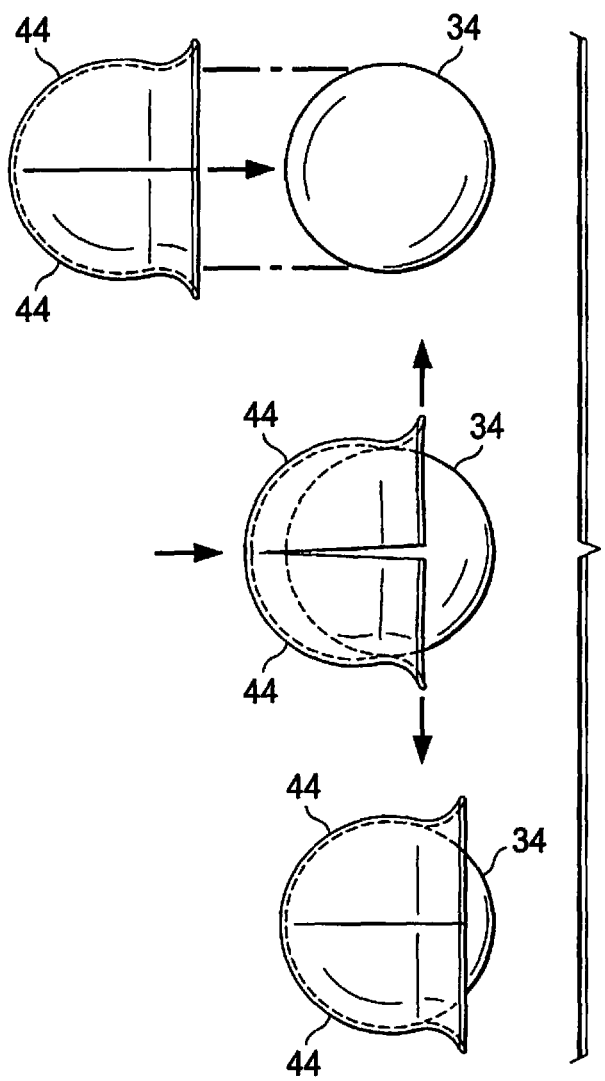
FIG. 4C is a side view showing an alternative binding system utilizing a ball and cup binder system in accordance with the present invention.

In an alternative embodiment depicted in FIG. 4C, articulating curved cup fingers 44 are shown with rounded lip edges shown on the circumference of the cup fingers 44 may help facilitate the connection process. In this embodiment, a spring mechanism (not shown) is employed to keep the cup fingers 44 in a closed position. Once the ball 34 is pressed into the cup fingers 44 with some force, the cup fingers 44 are pushed open by the ball 34. In this embodiment, the cup is formed by a plurality of cup fingers 44 with curved edges that can open or close as shown. Once the ball 34 has been pushed substantially into the cup formed by cup fingers 44, the cup fingers 44 may then close around ball 34 resulting in a connected binding system. Disengagement between the ball 34 and cup fingers 44 would typically occur in a reverse fashion. The force required to push the ball 34 into the cup fingers 44, or to pull it back out, can be designed to be appropriate for the situation of usage with low effort required by the operator for engagement and disengagement. It is contemplated that many combinations and derivatives of the binding functions discussed herein could be employed with the method and apparatus discussed herein using connection means and mechanisms that are known in the art.

FIGS. 4A-4C depict alternative binding systems utilizing the principles of male and female type components which when joined together create a securably detachable connection. However, it is contemplated that many different shapes, sizes and mechanisms for binding are commonly known in the art and the embodiments disclosed herein are not to be construed as limited as to those which have been disclosed, as such binding mechanisms are too numerous and diverse to be described herein. Likewise, in addition to "press and fit" style components that change their shape to attach and detach, other types of binding mechanisms may be used with the invention herein. For example, friction binding systems, hook and loop binding systems, and simple mechanical binding systems, such as with a hook and ring or snaps, could also be utilized as binding systems allowing for the operator to attach and detach from the radiation protection system.

Figure 4D:
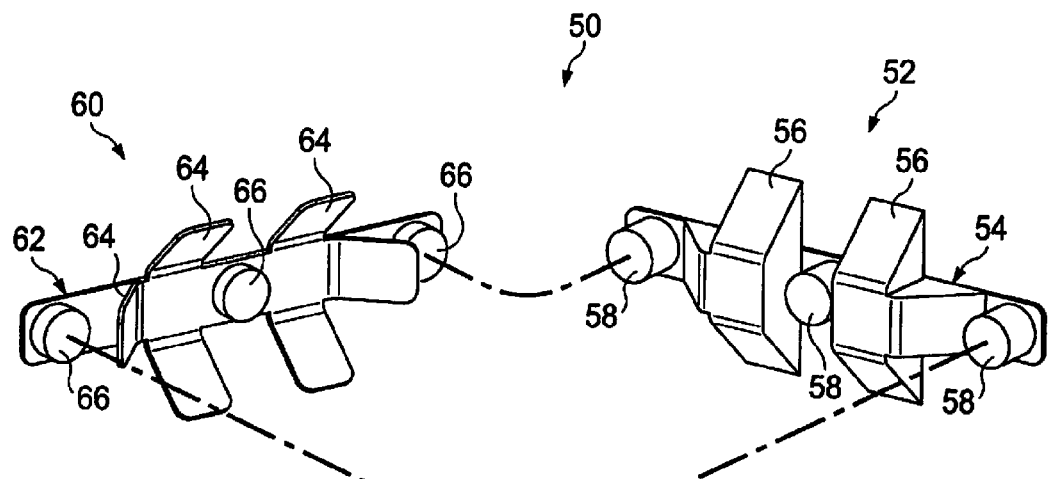
FIGS. 4D and 4E are perspective views showing an alternative integrated magnetic and mechanical binder system utilizing magnets and interlocking blocks and fingers shown in separated and interlocked positions, respectively, in accordance with the present invention.
Figure 4E:
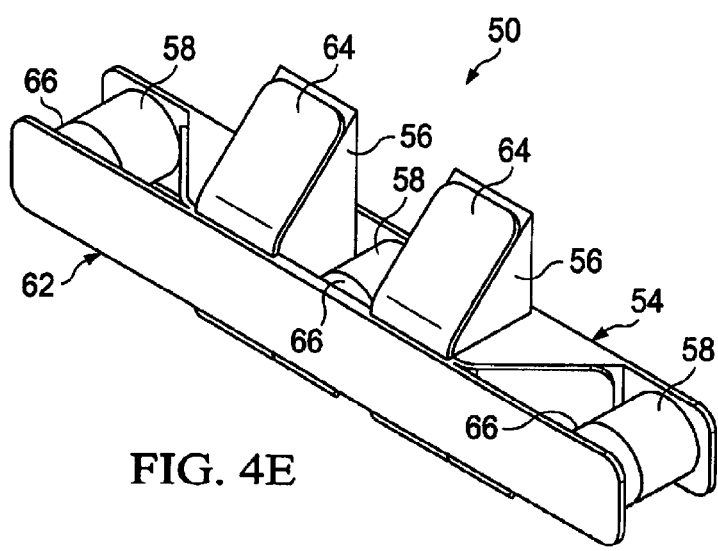

In another embodiment shown in FIG. 4D and FIG. 4E, a magnetic mechanical binding system 50 for binding the operator to the personal radiation protection system is shown. System 50 is composed of first binding component 52 and second binding component 60. First binding component includes base plate 54, one or a plurality of guide blocks 56, and one or a plurality of strike plates 58. Guide blocks 56 and strike plates 58 are secured to base plate 54 via various connection means as known in the art. Guide blocks 56 may consist of a variety of shapes, surfaces and materials with desired characteristics for forming a mating surface with the second binding component 60. The shapes and surfaces may be rigid, deformable, malleable, magnetic, or have multiple physical and mechanical characteristics which assist in forming a connection with the constituents of the second binding component 60. Second binding component includes base plate 62, one or a plurality of guide fingers 64, and one or a plurality of magnets 66. Guide fingers and magnets 66 are secured to base plate 62 via various connection means as known in the art. The shapes and surfaces attached to base plate 62 may be rigid, deformable, malleable, magnetic, or have multiple physical and mechanical characteristics which assist in forming a connection with the constituents of the first binding component 50.

Figure 4F:
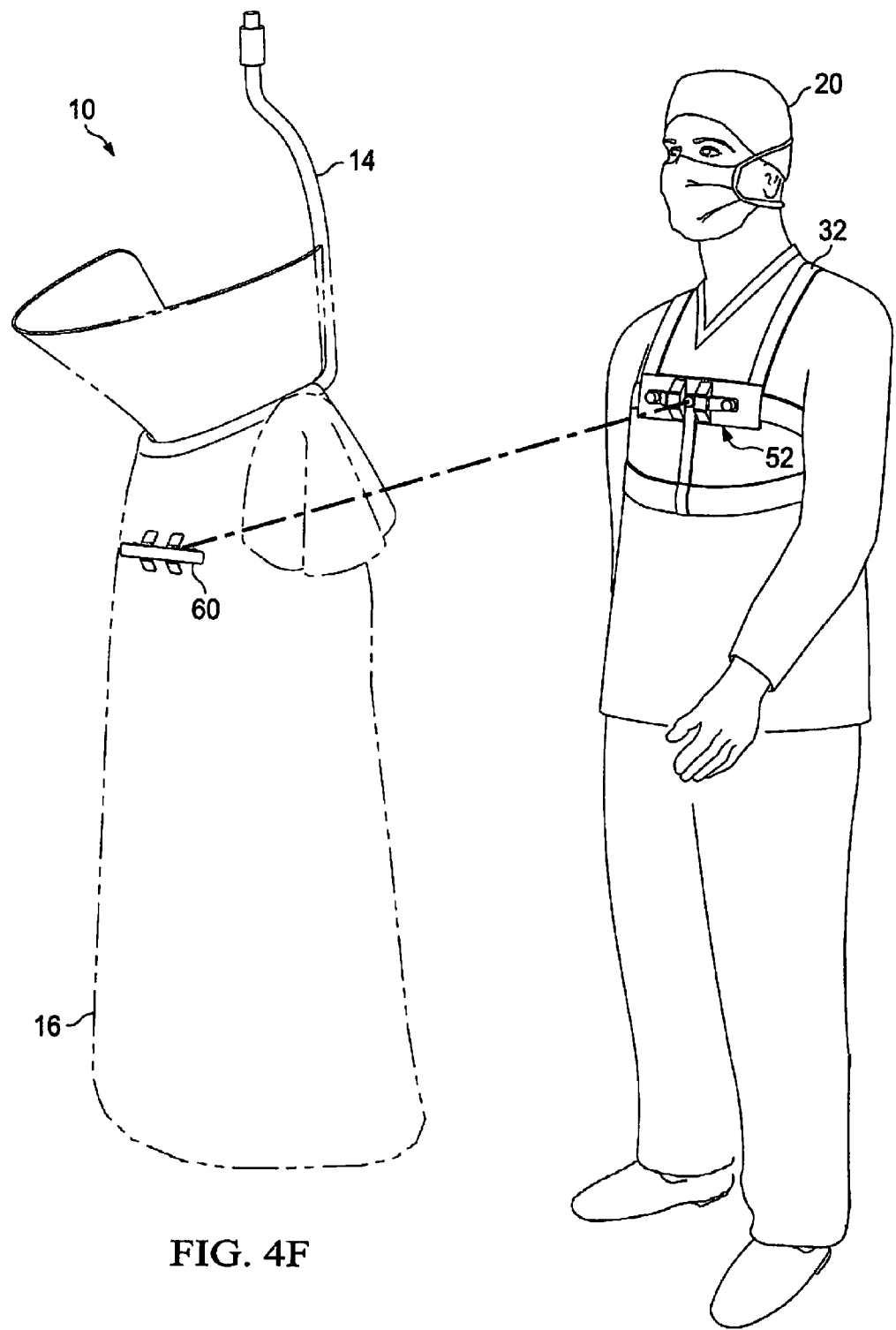
FIG. 4F is a perspective view of the magnetic mechanical binder system integrated with a harness on the user and with the personal radiation protection system in accordance with the present invention.

As depicted in FIG. 4D, guide fingers 64 orient at angles from the guide blocks 58. The guide blocks 56 and guide fingers 64 assist in guiding the first and second binding components 52, 60 together for forming a binding connection as shown in FIG. 4E. Referring to FIG. 4F, as the operator 20 moves in proximity toward the radiation protection system 10, the first and second binding components 52, 60 may not be on track to line up for mating and forming a secure connection. As such, the operator guides the first binding component 52, which in the embodiment shown is attached to the operator 20 via harness 32, towards the second binding component 60, which in the embodiment shown is secured to radiation protection system via garment 16, guide fingers 64 are positioned with the guide blocks 56, and as the magnetic attractive force between strike plates 58 and magnets 66 increases, the first and second binding components are mated together to form a sufficient mechanical magnetic binding.

First and second binding components 52, 60 are shown in the mated or connected position in FIG. 4E. Once engaged, the guide fingers 64 fit securely around in symmetry with the guide blocks 56. This serves to provide an additional mechanical binding component to the binding forces between the operator 20 and the radiation protection system 10, in addition to the magnetic binding forces described in this embodiment. For example, it prevents substantial translational motion of the base plates first and second binding components 52, 60 relative to each other. Such translational motion is also resisted by the magnetic force between the strike plates 58 and magnets 66. Thus the magnets 66 do not "slide" against the strike plates 58. Such a combination of magnetic force and mechanical forces is readily adaptable to this embodiment since they resist the inadvertent disengagement of the operator 20 from the system 10 during the performance of procedures. Nonetheless, intentional disengagement from the system 10 by the operator 20 is quite simply accomplished by a sudden, but not excessive, thrusting of the base plates 52, 54 directly apart from each other, such as is easily achieved by pushing the radiation protection system 10 away from the operator's body 20, which is a motion that is unlikely to occur inadvertently during normal use. In alternative embodiments, the magnetic binding system disclosed herein may be used without related guide plates, guide blocks or with additional mechanical connection components (e.g. snaps, hook and loop fasteners). In still other embodiments, the first or binding component may simply consist of one or more magnets fixed directly to the operator via a harness, belt or stitched directly to the operator's clothing, with the second binding component consisting of one or more strike plates fixed in a variety of locations on the system 10, including frame 14 and/or garment 14. Other embodiments may use the principles of magnetism or electromagnetism with or without mechanical forces using various shapes of magnets, shapes of guide fingers and guide blocks, or other mating or fastening means components as known in the art.

As shown in FIG. 4F, the operator 20 may don a harness 32 with a first binding component 52 secured to the harness 32 prior to gowning or after gowning which allows the operator 20 to position the first binding component 52 beneath or on the surface of the gown as desired. Once the harness 32 is donned by the operator 20 and the operator 20 is ready to engage with the radiation protection system 10, the operator guides the first binding component 52 into a mated position with second binding component 60. Once engaged, the operator 20 is then free to move in concert with the system 10 while performing a procedure. When the operator 20 is ready to disengage from the system 10, the operator 20 simply exerts enough force to overcome the binding force between the first and second binding components 52,60 thereby resulting in the separation of the operator 20 from the radiation protection system 10. Disengagement may be accomplished by the simple wave of the operator's hand, a push movement, a twisting movement or other bodily movement, allowing the operator 20 to exit the protection system 10 with little effort and maintaining sterility. If required, the operator 20 may disengage and reengage with the protection system 10 as described above without breaking sterility or the sterile field.

FIGS. 4D-4F depict various types of configurations utilizing magnetic and mechanical forces to enable engagement and disengagement of binding components. However, it should be noted that a plurality of different configurations of components could serve the same or substantially similar functions within the scope of this invention. For example, instead of using guide blocks and guide fingers as disclosed herein, any combination of male and female shapes could serve the same or similar purposes of stabilization and limitation of motion between the two binding components when engaged, and to enhance the magnet's function of keeping the components engaged as desired. Usually, the binding shapes could mate without requiring deformation, but deformable shapes could also be employed. For example, the shapes depicted herein will mate when brought directly together in a wide variety of spatial approaches; however, different designs might require special spatial approaches to enable engagement. The shapes depicted use guide fingers that are oriented at angles that facilitate guidance of the guide blocks into proper alignment as the blocks approach the fingers from a variety of spatial positions. The angles and shapes of the guiding mechanism could be highly variable. A large bowl-type shape could be used, and shapes that are triangular, hexagonal, octagonal, or any number of angular sides could be used. Smooth shapes or sharply angulated shapes may be used on one or both binding components as desired. The shapes depicted in FIGS. 4A-4C act to guide the binding components when approach between the binding components is off-center in any spatial direction. Nonetheless, more limited guiding mechanisms may be designed to provide re-orientation of the binding components when approach between them is off-center in certain directions. The binding components shapes and properties may also be designed to perform multiple functions. For example, the guide blocks and guide fingers serve to help guide components into a mated position together when they are approaching each other off-center, but they may also act to provide mechanical stabilization once the elements are engaged, by both limiting the range of motion between the engaged components, and by increasing the magnitude and force required to disengage the parts from each other. In alternative embodiments, it would be somewhat simple to change the configurations of binding components such that these different functions would be provided by different components (i.e. the guiding elements could be separate from the stabilization elements). Additional designs and embodiments incorporating these various approaches are contemplated, yet not described in detail herein due to the vast number of possibilities that will serve the same or similar purpose within the spirit and scope of this invention. As such, the disclosure herein is not to be construed as limited to only the embodiments shown herein.

In another alternative embodiment, the magnetic force between the strike plate 58 and magnet 66 shown in FIGS. 4D and 4E may be controlled with electromagnetic means as known in the art. Electromagnets may be activated and deactivated by the operator via a switch means attached to either the operator's harness, the radiation protection system, to a fixed location in the suite, or externally to the system by a wired connection or wireless control system. The operator may then simply position the first binding component in relative proximity to the second binding component, initiate an electromagnetic force, resulting in the engagement of the first and second binding components. When the operator desires to exit the protection system, the operator deactivates the electromagnetic force, resulting in the disengagement of first and second binding components and exits the protection system. Alternatively, activation of the electromagnetic force could cause detachment while de-activation causes engagement of the first and second binding components, through the use of mechanical means that are over-ridden by the electromagnetic force.

Many embodiments of the disclosed invention could be integrated with a locking mechanism, such as electromagnetic or clutch locking systems, for locking and unlocking the articulations or joints of the suspension assembly, thereby coordinating the operator's entry or exit from the system with the immobilization or partial immobilization of the entire system. For example, a locking mechanism may be incorporated into the system allowing the operator to de-activate the electromagnets in the binding system for the operator to exit the system, and this action could also actuate a switch that in turn activates the locking or clutch mechanism in some or all articulations or joints of the suspension assembly, resulting in the immobilization of the radiation protection system in a "parked" mode while the operator is free from the system, thereby preventing the system from moving and/or drifting into un-sterile territory.

In alternative embodiments, the quick release mechanism may be configured so as to provide for disengagement by the operator's hand movement or other body motion. The binding system disclosed herein may be positioned in the front, rear, or side of the garment and/or frame. The harness described herein may be secured to the operator by hook and loop fasteners, magnets, snaps, buttons, straps, buckles or any suitable fastening means known in the art. In another embodiment, the harness may be sterile, donned outside the operator's gown, and operable to mate with the binding component secured to the frame or garment through the sterile drape covering the garment or frame. In a similar fashion, a sterile belt or other retention means is utilized to mount the binding means attached to the frame or garment. In this embodiment, the binding system is sterile and mates without a gown or drape between the binding components.

In another embodiment, the operator wears a non-sterile harness under her sterile gown. After gowning, a second binding component, also sterile, is attached outside the gown, using magnetic or mechanical means to bond to the harness system through the operator's gown. This outer component is equipped with binding means to bond with a binding component on the device. It could bond to the device through the drape surrounding the device, or the device could, similar to the described system above, have a second, sterile binding component that binds to the device component through the drape, and said outer component would then bond to the component attached to the operator. Thus, the binding system could be composed of multiple binding components in layers, including layers of gown or drape to provide sterility during engagement and disengagement or re-engagement of the operator. This system may have advantage in allowing the mating components that are repeatedly engaged and disengaged, to oppose directly without interposed layers of sterile material. In alternative embodiments, the binding components may be located in front of, in back of, or in various locations around the circumference of the operator's person and the radiation protection system components.

Figure 5A:
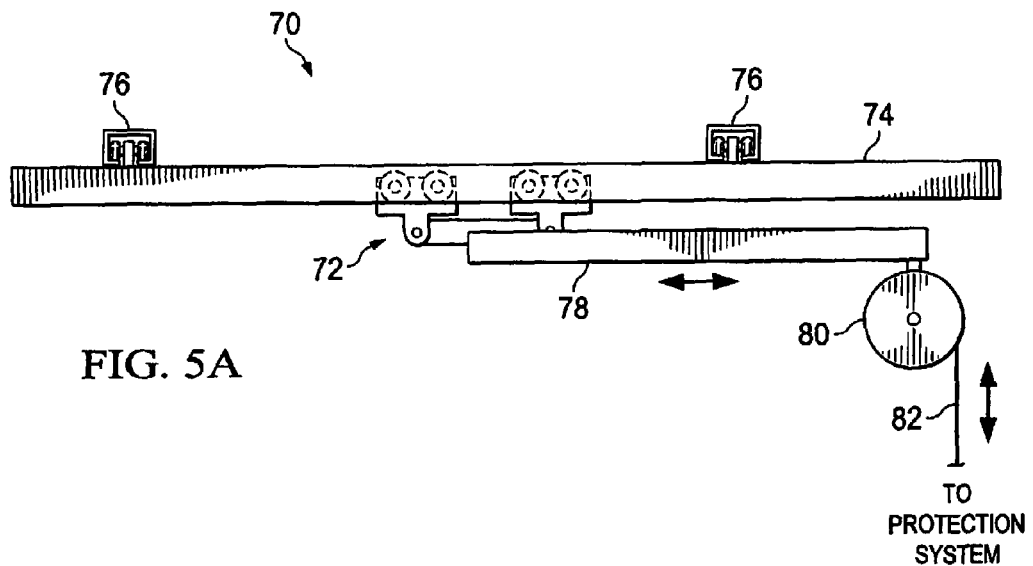
FIG. 5A is a side view of an extension arm in accordance with the present invention.
Figure 5B:
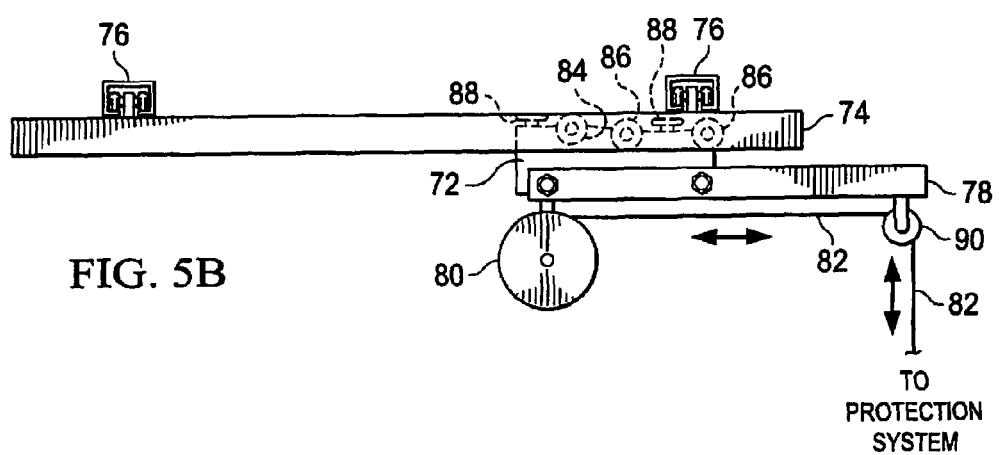
FIG. 5B is a side view of another embodiment of an extension arm showing the extended extension arm in accordance with the present invention.

FIGS. 5A-5C depict an embodiment of an improved extension arm assembly 70 utilized in connection with the personal radiation protection system disclosed herein. As described herein, a trolley 72 is a component of the system 70 which moves linearly along the Y axis in the horizontal plane along the bridge 74, and the bridge 74 may move linearly along the X axis in the horizontal plane along rails 76 of the system, which are attached to a structural support (e.g. ceiling) and provides an attachment site for assembly 70. The assembly 70 also includes an extension arm 78 attached to trolley 72. A balancer 80 may be fixedly attached or slidably attached to the extension arm 78 along with a wire rope 82. In an alternative embodiment, an articulated extension arm may be used (shown in FIG. 5C). The balancer acts to provide a supporting force for the protection system, by utilizing cables, springs, counterweights, pneumatic, electric or hydraulic systems as known in the art, which offer any of several degrees freedom of motion and provides substantial support for the weight of the protection system on the while providing for movement of the system in a substantially weightless manner. Extension arm assembly 70 may also include any number of articulating joints and arms as desired or required for specific applications.

Accommodating a bridge/crane setup may prove difficult in some applications, especially when rails 76 or bridge 74 cannot be positioned over an area where the suspended device may be usefully employed due to mounting limitations. In order to overcome these limitations, FIG. 5A depicts an extension arm that in the depicted embodiment is rigidly attached to the trolley 72. In one embodiment, the extension arm 78 extends beyond the patient table, extending the reach of the system 70 along a linear axis. In the embodiment depicted in FIG. 5B, anti-kickup wheels 84 are integrated with the trucks of trolley 72, in addition to trolley wheels 86, to counteract the additional torque on the trolley 72 and prevent "kick-up" of the trolley 72 and/or extension arm 78. Side wheels or rollers 88 may also be utilized in the trolley trucks to prevent sideways movement in the transverse plane to the lateral motion of the trolley 72.

FIG. 5B depicts the extension arm 78 with the balancer 80 positioned so as to provide some degree of counterbalance effect to the protection system weight transmitted by wire rope 82. In this embodiment, the balancer is placed underneath the trolley 72. Pulley 90 provides a rotational guide mechanism for wire rope 82 in this embodiment. This change in the position of the balancer 80 moves the center of gravity of the load suspended from the extension arm 78 closer to the trolley 72 center of gravity. This reduces the moment arm torque on the trolley 72 and the extension arm 78 and thus facilitates improved movement of the trolley 72 and reduces the structural requirements of the trolley 72 and extension arm 78, thereby decreasing the mass and overall weight of the system 70. As a result, less force is required by the operator to accelerate the system 70 by operator movement.

In another embodiment not shown, these advantageous effects can be enhanced further by positioning the balancer on an arm located on the opposite distal end of the trolley relative to the extension arm carrying the load. In these embodiments where the balancer is not directly over the supported load, the wire rope is dispensed through a system of pulleys or similar devices. Likewise in other embodiments, instead of a spring balancer, this same system could utilize other means of balancing the load such as pneumatic balancer, simple counterweights, springs, or any other means known in the art.

In an alternative embodiment not shown, the extension arm is attached to the trolley with a fixed pivot at one end of the extension arm. As a result, the extension arm may pivot freely in the horizontal plane so as to provide the operator with improved radial freedom of movement. This extra motion occurs at the expense of torque forces out of the plane of the trolley wheels, possibly requiring a wider base of support such as provided with the double girder bridge structure (as depicted in FIG. 1) and/or another set of trolley wheels in a different plane. Alternatively, the degree of motion radially could be limited so as to keep these disadvantageous forces minimized.

In the embodiment depicted in FIG. 5C, an articulated extension arm 92 is attached to trolley 72 and the radiation protection system 10 with a rotatable connection between rotation joint 96 and hanger 26. Articulating extension arm 92 articulates to allow vertical motion of the radiation protection device 10 while maintaining its vertical orientation. In this embodiment, the bridge 74 and trolley 72 permit free linear motion of the radiation protection device 10 in the horizontal plane and the articulating extension arm 92 provides for substantially linear motion in the vertical plane, while also including a spring balancer mechanism 94 for counteracting the weight of the suspended radiation protection device 10. A rotational joint 96 permits rotation of the radiation protection device 10 as shown. In this way, translational motion of the device 10 is permitted anywhere in the spatial volume of the X, Y and Z axes, while rotational movement of the device 10 in the vertical planes is precluded.

In the lower figure of FIG. 5C, the trolley 72 and extension arm 92 are shown as having moved outside of bridge rails 76 and the articulating extension arm 92 is in a lowered orientation as shown. Thus, the radiation protection device 10 has translated in the x and z spatial axes relative to the top figure shown in FIG. 5C, and could easily also translate in the Y axis through movement of the bridge 74 along rails 76. Other alternative embodiments may provide any number of additional degrees of freedom of motion, including rotational motion of the radiation protection device in different planes to alter the protection system orientation as needed, such as to provide pitch and roll, by using a swivel joint. Such motion may occur in the absence of translational motion of the bridge and trolley components. Any number of articulations may be provided in the extension arm system or in the hanger and/or frame to enable the desired effect.

FIGS. 6A-6F depict one embodiment of an adjustable face shield system 100 which may be integrated with the personal radiation protection system disclosed herein. When performing procedures, the operator will commonly stand on one side of the patient table. Typical suites are designed asymmetrically so that one side of the patient table provides a better proximity to optimize the available lighting, shielding, controls, back table supplies, and space. The remaining space surrounding the patient table is usually available to the operator, although typically with some limitation.

For most common procedures, the operator tends to receive greater radiation exposure on the left side versus frontal exposure, while the operator's right side typically receives the least amount of scattered radiation while conducting a procedure on a patient. The geometry is such that a shield oriented to the left, front side of the operator provides optimal protection. The configuration may be changed however, when the operator moves to the opposite side of the patient table to conduct a procedure.

Figure 6A:
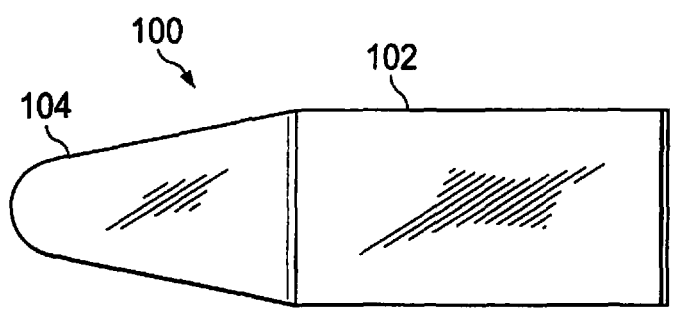
FIG. 6A is a front view of the face shield in accordance with the present invention.

Various example embodiments of an adjustable face shield assembly 100 are depicted in FIGS. 6A-6E. The shield may be manufactured from lead acrylic, lead glass, or other radio protective materials that are significantly transparent to visible light. FIG. 6A is a front side view depicting a face shield assembly 100 with a front plate 102 and a side plate 104. The front plate 102 and side plate 104 may be provided with beveled edges so as to allow the front plate 102 and side plate 104 to be positioned together at an angle to provide a unified barrier. In one embodiment, the front plate 102 is positioned directly in front of the operator's face, while the side plate 104 is positioned at an angle to the operator's face.

Figure 6B:
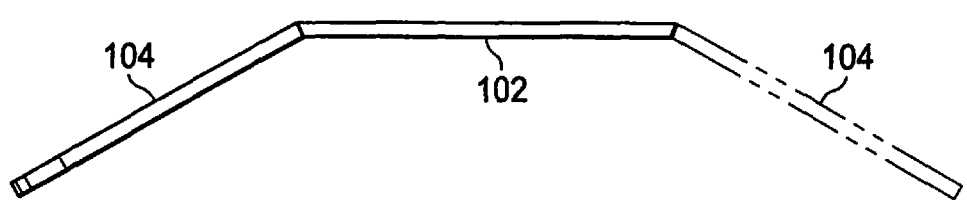
FIG. 6B is a top view of the face shield in accordance with the present invention.

FIG. 6B depicts an alternative embodiment of the shield wherein the side plate 104 may include beveled edges on opposite sides, so that it may utilized on either the right or left side of the front plate 102 depending on the operator's position. This embodiment allows the operator to remove a side plate 104 from the one side, and affix it relative to the opposite side of the front plate 102, by simply inverting the side plate 104 and securing it to the frame 14. This precludes the necessity of having a "left" and "right" side plate, as one side plate 104 may be utilized as a "left" or "right" side plate at the behest of the operator and the orientation of the system to the patient table.

Figure 6C:
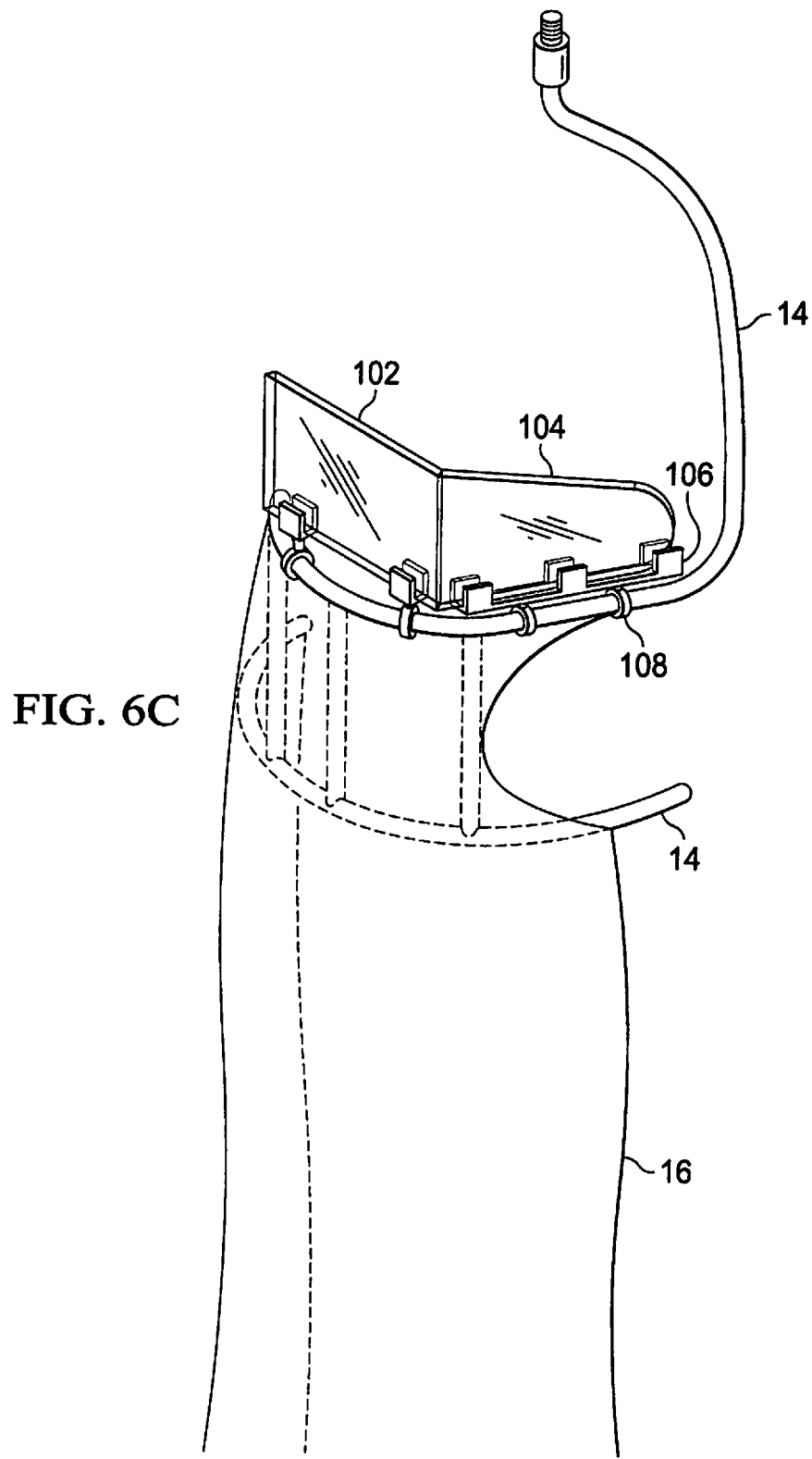
FIG. 6C is a perspective view depicting the hanger, face shield and frame in accordance with the present invention.

As shown in FIG. 6C, shield plates 102,104 are shown detachably secured to the frame 14 via shield retention bar 106. Shield plates 102,104 may be secured to the frame 14 using friction type fasteners, such as rubber grommets or other known fasteners that provide a sufficient grip between the shield retention bar 106 and shield plates 102,104. Shield retention bar 106 may be detachably secured to frame 14 via clamps 108. Clamps 108 may include clamping means that are well known in the art, such has screw clamps, hose clamps, or other reliable clamp fittings. In alternative embodiments, the shield retention bar 106 may be integrated directly with the frame 14 or welded thereto, or clamps 108 may also be utilized to attach garment 16 to frame 14. The side plate 104 may be detachably secured to either the left or right of the front plate 102, thereby allowing the operator to adjust the shield configuration to her preference. Multiple shield plates may be designed or shaped to provide protection to the operator in a variety of operational environments or the preferences of the individual operator.

Figure 6D:
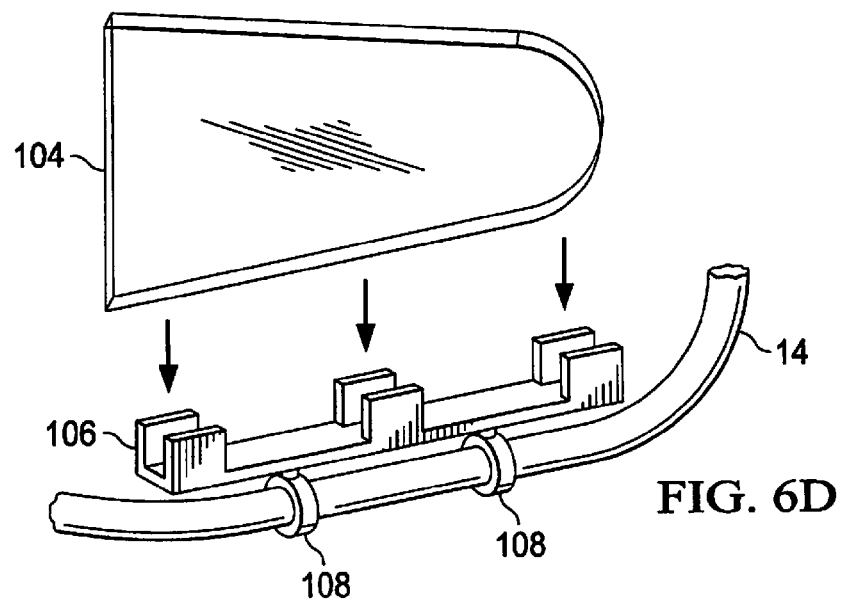
FIG. 6D is a perspective view showing the face shield attachment and adjustment mechanism attached to the frame in accordance with the present invention.

FIG. 6D depicts another embodiment of the adjustable shield disclosed herein. A shield retention bar 106 is shown detachably secured to the frame 14. Retention bar 106 is secured to the frame 14 via clamps 108. Retention bar 106 may be fabricated out of metal, rubber, polymers, ceramics or any material capable of supporting and retaining the face shield plates, in the depicted embodiment side plate 104. Retention bar 106 provides a detachable connection for securing the shield plates 102,104 to the frame 14. In the depicted embodiment, the operator simply slides the shield plate 104 into the retention bar 106 where the friction or retention force in bar 106 retains the shield plate 104 in the desired position. The operator may move the shield plate 104 along the retention bar 106 as desired for placement and protection.

Figure 6E:
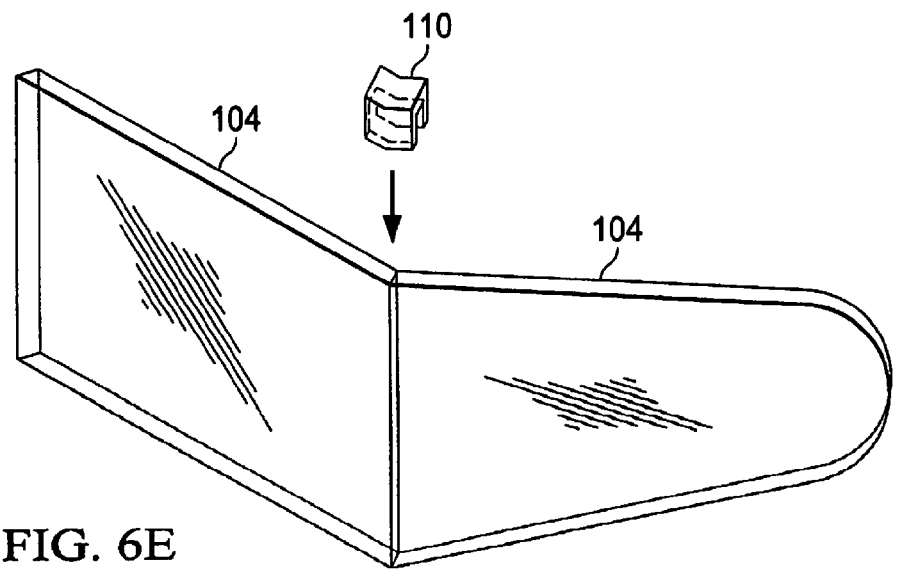
FIG. 6E is a perspective view showing an alternative face shield attachment and adjustment mechanism in accordance with one embodiment of the present invention.

A shield connector 110 is shown in FIG. 6E wherein the top portion of the front shield 102 and side shield 104 may be further secured relative to one another by means of a connector 110. Connector 110 may be constructed of rubber, nylon or other suitable material capable of maintaining a friction connection that may be affixed at the top or side edges of the shield plates 102,104 where they are in close proximity to keep the shield plates 102,104 in position relative to one another. Connector 110 may also be used if side plate 104 was inverted and moved to the right side.

Figure 6F:
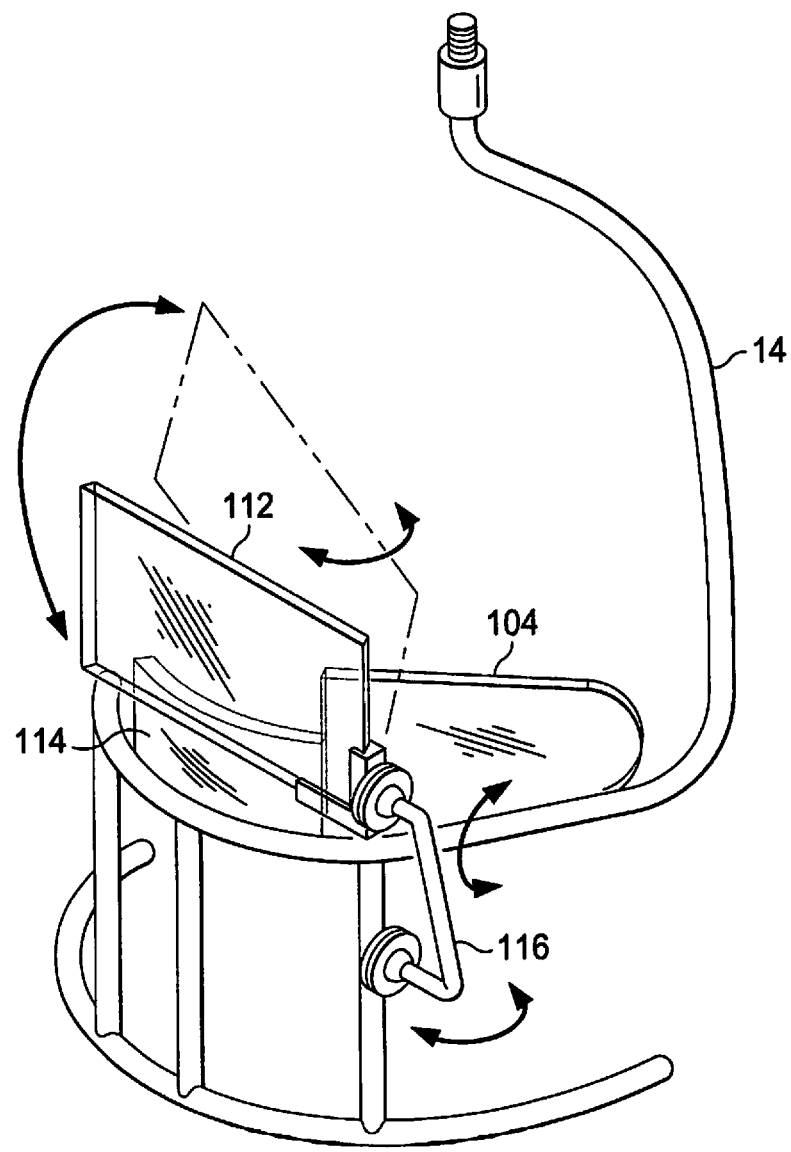
FIG. 6F is a perspective view showing the adjustable features of the face shield in accordance with one embodiment of the present invention.

FIG. 6F is a depiction of an alternative embodiment where the shield 112 or a portion of a modular shield, is secured to the frame 14 via arm 116. As depicted, a side shield 104 is affixed to the frame 14. Similarly, a small front shield 114 with a low height is fixed to the front of the frame 14 and is held in a substantially fixed position. Shield 118 is attached to the frame 14 by an arm 112 that in some embodiments has flexible joints, pivots, or hinges at each end, where it attaches to the frame 14 and where it attaches to the shield 118. The flexible joints, which comprise a ball-in-socket joint in the embodiment shown, provide many degrees of freedom of motion. The front shield 118 can be manipulated and moved by the operator to a desired position in all spatial planes. For example, the front shield 118 may be positioned outside of the operator's line of sight when performing a procedure where vision is critical and shielding by the front shield 118 is not required. Arm 112 allows the operator to adjust the attached shield 118 or additional shield plates (not shown) to the optimal orientation for protection and/or glare reduction.

The shield system described herein may be secured to the frame by friction connection means, rigid means, by an extension arm assembly, or by other means as is known in the art. In one embodiment depicted in FIG. 6G, a single piece curved shield 18 may be slidably connected to frame 14 along a sliding track integrated with frame 14. The operator 20 may simply move the shield 18 along the curvature of the frame 14 with her hand, while shield 18 remains in position with the frame 14. Such capability makes it simple for the operator 20 to move the shield 18 position, to reduce glare from the shield and/or to improve radiation protection to the operator 20 due to angle of scattered radiation during a particular procedure. This embodiment allows the operator 20 to quickly and easily move the orientation of the shield 18 without the need to detach or physically detach and reattach the shield 18 from the frame 14. Likewise, the orientation and position of the shield 18 may benefit from occasional repositioning during an actual operation with a patient, while allowing the operator 20 to move and/or manipulate shield 18 while remaining sterile.

In alternative embodiments, any number of shield plates may be attached to the frame at various locations on the frame as desired by the operator or as required by the procedure. Alternate embodiments could involve more than 2 flexible joints per arm. For example, an articulated arm with a joint in its middle section could be used for increased freedom of motion. Alternate embodiments could include any number of movable or stationary shield components slidably connected to the frame as discussed above. Also, any type of joint is possible, with any different number and combination of degrees of freedom of motion. A flexible arm system, or "snake" as is sometimes used with common table lamps, could be utilized. Other embodiments may not utilize fixed shield components, and all components could be movable on flexible joints or arms. Other embodiments may utilize one large, curved or angled shield, or flat shield, on a flexible attachment that can be moved about by the operator to provide optimum shielding and glare reduction. In another embodiment, a handle mechanism may be fashioned for attachment to a portion of the shield or arm to allow movement of the shield by sterile hands of operator without contamination. Alternatively, a sterile cover or drape may cover a portion of the moving system to allow such manipulation.

FIG. 7 depicts an embodiment of the personal radiation protection system disclosed herein with a lighting apparatus attached therewith. During the conduct of a procedure, lamps or other lighting means are used to facilitate the conduct of the procedure. As can be imagined, sufficient lighting must exist in the suite so that the operator may skillfully and safely conduct a procedure. Ideally, the lighting mechanism is powerful, capable of being manipulated for optimum direction, and have a broad reflective base to provide a wide beam of light with minimal shadowing. In some procedures, the operator conducts the procedure by viewing a monitor which projects images received from camera feeds.

In some operational suites where space is confined and at a premium, it would be preferable to utilize a smaller lighting source which may be attached to the system disclosed herein. As shown in FIG. 7, one embodiment of the invention disclosed herein includes a lamp or light source 120 connected with the frame 14 via arm 122. A manipulation handle 124 may be included which allows the operator to adjust the direction of the light source 120 with a simple hand movement, while allowing the operator to maintain optimum light direction on the subject. Alternatively, lamp 120 could be connected directly to the frame 14, garment 16, face shield 102, side shield 104 or any portion of the system generally described herein.

Light source 120 may also be integrated with the system disclosed herein so that its weight may be used as a counterweight, providing an additional mechanical advantage to the entire radiation protection system. Light source 120 may be positioned in a variety of positions relative to the operator as desired. Light source 120 may be powered by typical electrical means integrated within the system as is known in the art. In one embodiment, light source 120 may be battery powered and therefore wiring and electrification of the system, or a portion of the system, would not be required. Batteries to power the light source 120 may be rechargeable, so that charging is performed during periods when the system may not be in use.

In addition to lighting systems, other alternative embodiments may include environmental controls such as fans or air blower/heater systems integrated with personal radiation system disclosed herein. Such environmental control systems may be affixed to the suspension assembly, frame, garment or any other component of the system disclosed herein. For example, a personal fan 121 may be attached to the frame 14 such that it circulates air on the operator. As with the light source 120, the environmental control system 121 may be powered by typical electrical means integrated with the system as is known in the art. In one embodiment, the environmental control system 121 may be battery powered and therefore wiring and electrification of the system, or a portion of the system, would not be required. Batteries to power the environmental control system 121 may be rechargeable, so that charging is performed during periods when the system may not be in use. FIG. 7 also serves to depict a frame embodiment wherein the frontal frame element sweeps around the lower head, neck, or upper torso region of the operator, but does not contain a lower frame below it. Instead, the garment hangs or is supported entirely from the upper frame element. In this embodiment, the left arm protrudes through an arm hole. Instrument holders are also depicted, providing places for storage of instruments, tools, or other objects used by the operator during tests or procedures. For example, a permanent magnet 105 may be attached within the garment and may be used during procedures as a storage or resting place for magnetic tools. Further, a tray 103 is depicted as being detachably secured to the frame assembly 14 and may be used to hold instruments or other objects as desired by the operator.

Figure 8:
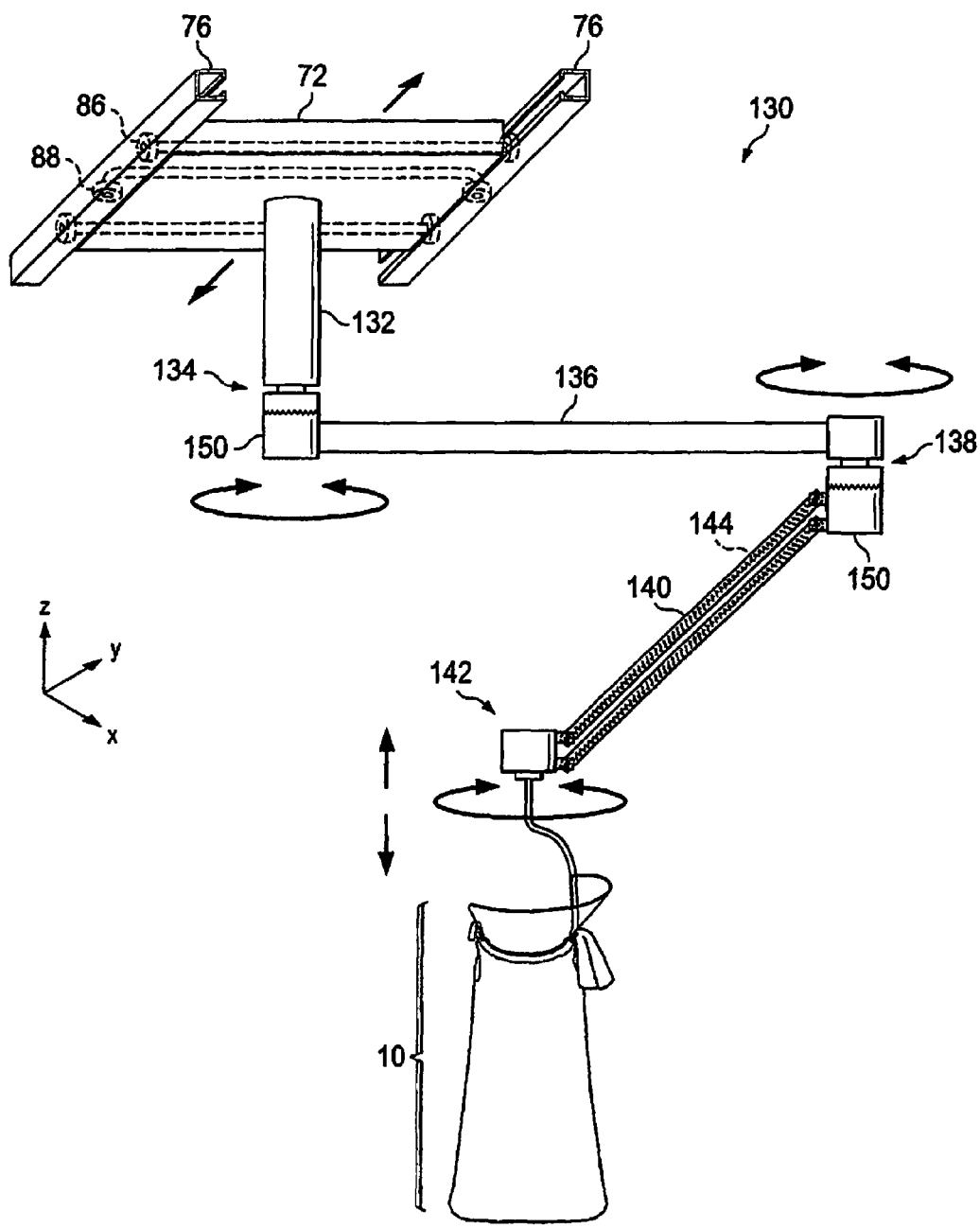
FIG. 8 is a perspective view of a manipulator arm suspension system integrated with a bridge and trolley system in accordance with one embodiment of the present invention; and, FIG. 9 is a perspective view of a manipulator arm suspension system attached to a fixed support with an alternative shield system in accordance with one embodiment of the present invention.

FIG. 8 depicts an alternative suspension system 130 which may be utilized with the personal radiation protection system disclosed herein. Suspension system 130 includes a post 132 attached to a moveable crane system including a bridge/trolley 72 that can roll linearly along the Y axis on wheels 86 and side wheels 88 within ceiling rails 76 as shown. In alternative embodiments, the suspension system 130 may simply be attached to a fixed point such as a wall or ceiling, for example by attachment of post 132 directly to the ceiling. In the embodiment shown in FIG. 8, the bridge/trolley 72 may be locked in position relative to the ceiling rails 76 when only suspension arm motion is desired. A first arm 136 is connected to post 132 such that it is oriented horizontally and may rotate in the horizontal plane, parallel to the plane of the floor about joint 134. A second extension arm 140 is connected to the first arm 136 via joint 138 and is operable to rotate in the horizontal plane about second joint 138 which allows rotation of extension arm 140 in the vertical plane. Extension arm 140 is operable to rotate in the vertical direction as well and operates to articulate in the vertical plane with spring tensioners 144 assisting in supporting radiation protection system 10 connected therewith via joint 142. Joint 142 allows rotation of the radiation protection system 10, for example a "spinning" or "twisting" motion of the radiation protection device 10, as might occur when the operator moves, turns or pivots. Joint 142 may also be configured to allow rotation in the vertical plane of the of the second arm 110 relative to frame 14. However, the second arm 140, joint 138, and joint 142 may be designed in certain embodiments to prevent rotation of the radiation protection device 10 in the vertical planes of space, thus preventing pitch or roll of the system 10. As a result, the radiation protection system 10 is operable to translate in all X, Y and Z spatial directions due to the rotational capability of joints 134,138,142, and to "twist" or experience yaw, without tilting, or experiencing pitch or roll. This freedom of movement may also be accomplished by the use of linkages in reaction arms, torque arms, and manipulator arms, commonly known in the art to provide such function and which are frequently used for suspended lamps, tools and other objects. Pitch and roll motion of the radiation protection device 10 can easily be allowed by the addition of joints in the arms 136, 140, or in the radiation protection system 10, as may be imagined in alternative embodiments. In alternative embodiments, the linkages at the ends of the first arm 136 may also integrate balancing mechanisms, springs and/or cables that offset the weight of the radiation protection system 10 and maintain the system 10 in the orientation that is set by the operator. Altogether, the disclosed system 130 permits positioning of the radiation protection system anywhere in the X, Y and Z space defined by the geometries of the arms and their motions.

In another embodiment not shown, a third arm may be removably secured directly to the frame supporting the radiation protection system with either a fixed connection or flexible connection as is known in the art. In other embodiments, additional joints will connect these structures to provide various desired degrees of motion therein. In still other embodiments, a plurality of joints and arms may be configured as desired. The joints may provide any combination of degrees of freedom as to movement in the X, Y and Z planes and various balancing means may be utilized with the system. Examples of such variations may include arms with multiple joints each allowing radial motion in the horizontal plane, with numerous short arms or "links" as in a bicycle chain restricted to movement in a "sidewinding" motion. The arms would thus all be oriented horizontally, and permit great freedom of motion in the horizontal plane with less limitation than a single, double or triple arm system. The radiation protection system could be suspended by a spring balancer with wire ropes or other means such as a balancing arm at the terminus. Alternatively, a manipulation system is envisaged with multiple arms, links, or segments with balancing mechanisms built into each linkage, or some of the linkages, along with several degrees of freedom in the linkages to allow vertical motion, so that the end of the arm system can move in the vertical as well as horizontal planes, and a spring balancer with cable is not necessary to keep the load balanced. Such a system may provide more flexibility and an increased range of motion.

In still another embodiment of the disclosed invention, it may prove desirable to have the ability to secure the radiation protection system to a fixed point or "park" or store the system while it is not in use. An internal lock system may be provided which places all or some of the joints in the system described in FIG. 8 in a locked position by the provision of frictional force or an actual mechanical locking mechanism. This force may be applied via clutches, friction plates, mechanical locks, electromagnetic force or by other means as known in the art at joints 134,138,142. Such a parking mechanism may be integrated with the binding system disclosed previously such that activation of the park mechanism is nearly simultaneous with disengagement of operator from system, and re-engagement by the operator de-activates the park mechanism for return of free motion.

Figure 9:
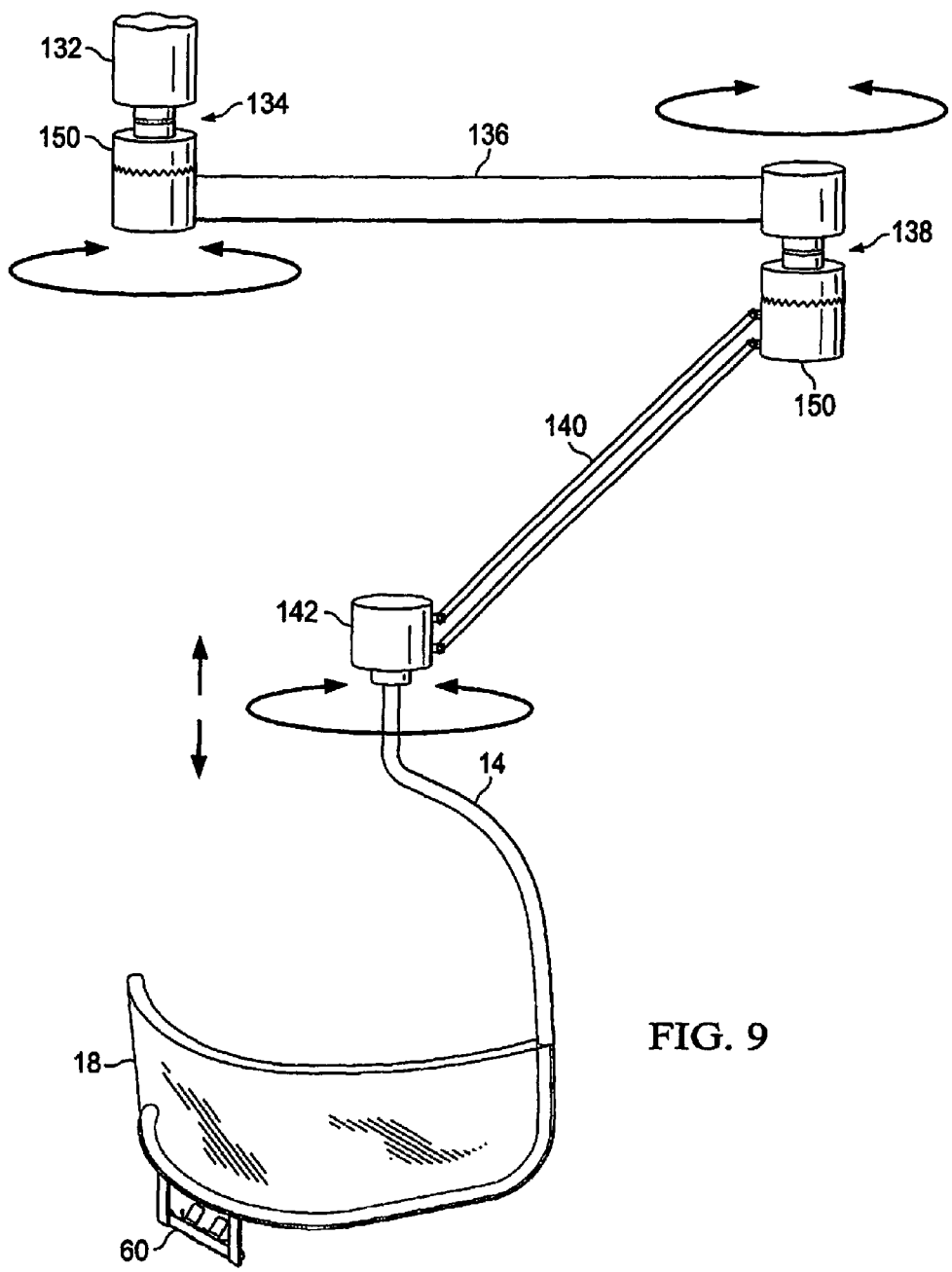

For example and with reference to FIG. 8 and FIG. 9, electromagnets may be positioned at any or all of the joints 134,138,142 connecting post 132 and arms 136,140, as well as being integrated in appropriate positions within the bridge/trolley 72. The entire system is then placed into an appropriate storage position and a sufficient electrical current may then be applied causing the electromagnets 150 located at or near joints 134,138,142 and/or within the bridge/trolley 72 act to form a sufficient binding force preventing the movement of each desired joint or component. In an alternative embodiment, a transient force may be initiated to activate a mechanical lock for each respective joint 134,138,142.

In another embodiment not shown, the operator may desire to place the personal radiation protection device in a stationary, fixed position while performing a procedure. The operator may simply park the device in a fixed position by actuating the electromagnetic system described above thereby fixing the personal radiation protection system in a fixed position. When the operator desires to move the device, she may simply disengage the electromagnetic force by activation/deactivation of a switch or other controller means, allowing the personal radiation protection system to freely move at the operator's discretion. Various components of the system may be fitted with such locking devices, so that only certain joints or components of the entire system may be placed in a fixed or unfixed position as desired.

Other systems may be utilized for keeping the device immobilized. A magnetic system may be used, whereby a magnet is present on the patient table, a portable stand, or the operator's back table. This magnet could engage a metallic strike plate affixed to the radiation protection device when it is placed in proximity, and would function even through the sterile drapes located on the various devices and equipment. The magnet could be sterile, or covered in a sterile cover or drape. Alternatively, the positions of the magnet and strike plate could be reversed, or magnets could be used in both positions. Other embodiments could use mechanical fastening means other than magnets, such as hook and loop fasteners, mechanical hooks, or any other systems widely known in the art. These could be covered with sterile drapes or provided in a sterile condition for use.

FIG. 9 depicts an alternative embodiment of the invention described herein, where the radiation protection garment may be omitted entirely from the system, which would be modified to provide an optimum platform for the suspension of the face and upper torso shield only. FIG. 9 depicts an alternative embodiment where frame 14 is supported by a suspension system including post 132, arm 136, and articulating extension arm 140 in a manner that maintains orientation of the frame 14 and shield 18 relative to the operator. Joints 134, 138,142 provide rotational connections as described herein allowing the system to move in the desired planes of motion. When using such a device, protection of the operator's torso and extremities would be provided by some other protection means such as a standard apron worn by the operator or other shield device. This might be desired by an operator who does not mind wearing and supporting the conventional heavy lead apron, or who prefers not to have the previously described suspended garment system for any reason such as any notion of encumbrance. This suspended system would be much lighter without the garment and could be supported by lighter and less expensive suspension apparatus. The depicted embodiment includes a transparent shield 18 that curves around the sides and front of the operator's head and upper torso, permitting free operator arm motion. In one embodiment, the shield 18 may be connected to a frame 14 that sweeps under the shield 18 as shown in FIG. 9, or alternatively frame 14 could support the shield 18 along the top margin of the shield 18, or the frame 14 could attach to the left or right side of the shield 18, or to another frame component that surrounds the shield 18 like a window frame. Shield 18 may be rigidly, slidably attached or movably attached to frame 14 as described herein.

In the embodiment shown in FIG. 9, the frame 14 may include a binding component, such as first binding component 54, for use with the magnetic binding system disclosed herein. In other embodiments, frame 14 may have one or more articulations within it to provide motion in any direction, or to change the orientation of the shield 18. Frame 14 may be structured to accept a sterile drape to maintain sterility of the operator when in proximity to her, and when the operator must grasp frame 14 to move it. Frame 14 may also include a handle to assist in moving or manipulating frame 14. In other alternative embodiments, the system disclosed herein may employ some or all of the possible functions, accessories and suspension means described in this document.

While the invention has been particularly shown and described with reference to certain embodiments, it will be understood by those skilled in the art that various changes in form and detail may be made therein without departing from the spirit and scope of the invention.

I claim:
1. A protection apparatus, comprising:
   a garment operable to protect an operator from a substantial portion of radiation;
   a frame with an open back permitting the operator to approach the frame without manipulating the frame and wherein the frame is operable to support the garment; and, a suspension assembly operable to support the weight of the frame and garment relative to the operator.

2. The apparatus of claim 1 wherein the suspension assembly is one selected from a group of components consisting of:
   a) a trolley;
   b) an articulating arm;
   c) a balancer;
   d) a reaction arm;
   e) an extension arm;
   f) a jib crane;
   g) a wire rope; and,
   h) a bridge crane.

3. The apparatus of claim 1 further comprising:
a rotating joint connecting the suspension assembly and the frame operable to allow the frame to rotate relative to the suspension assembly.

4. The apparatus of claim 1 further comprising:
an instrument holder detachably secured to the garment, the frame, or the suspension assembly.

5. The apparatus of claim 1 further comprising:
a shield slidably connected to the frame along a sliding track integrated into the frame and operable to allow the operator to move the shield.

6. The apparatus of claim 1 further comprising:
an arm with at least one flexible joint attached to the frame; and,
a modular shield attached to the arm.

7. The apparatus of claim 1 further comprising:
a shield retention bar attached to the frame; and,
a front plate or a side plate attached to the shield retention bar.

8. The apparatus of claim 1 further comprising:
a shield retention bar attached to the frame; and,
a face shield assembly attached to the shield retention bar, wherein the face shield assembly includes a front plate and a side plate, wherein at least one of the front plate or side plate includes a beveled edge so that the front plate and side plate may be positioned to form a substantially unified face shield.

9. The apparatus of claim 8 further comprising:
a shield connector attached to an edge of the front plate and an edge of the side plate.

10. A protection apparatus, comprising:
a garment operable to protect an operator from a substantial portion of radiation;
a suspension assembly operable to support the weight of the garment relative to the operator; and,
a binding assembly operable to engage the operator and protection apparatus with one another wherein the binding assembly includes a binding component attached on or about the operator's person or the garment.

11. The apparatus of claim 10 further comprising:
a frame with an open back permitting the operator to approach the frame without manipulating the frame and wherein the frame is operable to support the garment.

12. The apparatus of claim 11 further comprising:
a rotational joint connecting the suspension assembly and the frame operable to allow the frame to rotate relative to the suspension assembly.

13. The apparatus of claim 11 further comprising:
a shield slidably connected to the frame along a sliding track integrated into the frame and operable to allow the operator to move the shield.

14. The apparatus of claim 11 further comprising:
an arm with at least one flexible joint attached to the frame; and,
a modular shield attached to the arm.

15. The apparatus of claim 11 further comprising:
a shield retention bar attached to the frame; and,
a front plate or a side plate attached to the shield retention bar.

16. The apparatus of claim 15 further comprising:
a shield connector attached to an edge of the front plate and an edge of the side plate.

17. The apparatus of claim 11 further comprising:
a shield retention bar attached to the frame; and,
a face shield assembly attached to the shield retention bar, wherein the face shield assembly comprises a front plate and a side plate wherein at least one of the front plate or side plate includes a beveled edge so that the front plate and side plate may be positioned to form a substantially unified face shield.

* * * * *